United States Patent [19]

Bundgaard et al.

[11] Patent Number: 4,694,006
[45] Date of Patent: Sep. 15, 1987

[54] ACYL- OR ACYLOXYMETHYL-ALLOPURINOL PRODRUGS

[75] Inventors: Hans Bundgaard, Horsholm; Erik Falch, Vedbaek, both of Denmark

[73] Assignee: A/S GEA, Copenhagen, Denmark

[21] Appl. No.: 711,583

[22] PCT Filed: Jun. 19, 1984

[86] PCT No.: PCT/DK84/00057

§ 371 Date: Feb. 26, 1985

§ 102(e) Date: Feb. 26, 1985

[87] PCT Pub. No.: WO85/00368

PCT Pub. Date: Jan. 31, 1985

[30] Foreign Application Priority Data

Jun. 30, 1983 [DK] Denmark ................... 3028/83

[51] Int. Cl.⁴ ............... A61K 31/505; C07D 487/04
[52] U.S. Cl. ........................... 514/258; 544/243; 544/262; 544/302
[58] Field of Search ........... 544/262, 243, 302; 514/258

[56] References Cited

U.S. PATENT DOCUMENTS

| | | | |
|---|---|---|---|
| 2,868,803 | 1/1959 | Druey et al. | 544/262 |
| 3,474,098 | 10/1969 | Hitchings et al. | 544/262 |
| 3,828,043 | 8/1974 | Kay et al. | 544/302 |
| 4,443,435 | 4/1984 | Bodor et al. | 544/302 |
| 4,460,590 | 7/1984 | Möller | 514/258 |
| 4,555,579 | 11/1985 | Rovnyak | 544/243 |
| 4,565,868 | 1/1986 | Verheyden et al. | 544/276 |

FOREIGN PATENT DOCUMENTS 468712  5/1969  Japan ................... 514/258

OTHER PUBLICATIONS

Bansal et al., *J. Pharm. Science*, vol. 70, No. 8, Aug. 1981, pp. 855–857.
Beauchamp et al., *J. Med. Chem.*, vol. 28, pp. 982–987, (1985).
Hussain et al., *J. Pharm. Science*, vol. 63, No. 5, May 1974, pp. 798–799.
Chu et al., *J. Med. Chem.*, vol. 18, No. 2, pp. 161–165, (1975).
Wermuth, C. G. from *Drug Design: Fact or Fantasy*, G. Jolles and, K. R. H. Woolridge, ed., (1984), (Academic Press, London), p. 68.
Bergmann et al, *J. Chem. Soc.*, Perkin I, pp. 2795–2802, (1979).
Bundgaard et al, *Intl. J. of Pharmaceutics*, vol. 23, pp. 223–237, (1985).
Bundgaard et al, *Intl. J. of Pharmaceutics*, vol. 24, pp. 307–325, (1985).
Bundgaard et al, *Intl. J. of Pharmaceutics*, vol. 25, pp. 27–39, (1985).
Bundgaard et al, *Acta. Pharm. Suec.*, vol. 18, pp. 129–134, (1981).

*Primary Examiner*—Donald G. Daus
*Assistant Examiner*—M. Noel
*Attorney, Agent, or Firm*—Birch, Stewart, Kolasch & Birch

[57] ABSTRACT

Compounds of the formula Ia and Ib

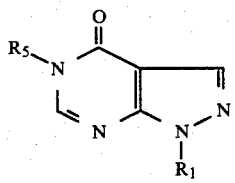

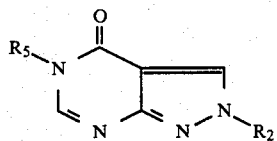

are prodrugs of allopurinol and have i.a. a much higher solubility in water and/or a higher lipophilicity than allopurinol, which makes such compounds useful for oral, parenteral and rectal administration to a warm-blooded animal such as a human. Such compounds will after administration be converted into allopurinol.

17 Claims, 5 Drawing Figures

ACYL- OR ACYLOXYMETHYL-ALLOPURINOL PRODRUGS

BACKGROUND OF THE INVENTION

1. Field of the Invention

The present invention relates to novel transient prodrug forms of allopurinol useful in the prevention and treatment of hyperuricemia, to methods for preparing the prodrug forms, to pharmaceutical compositions containing such prodrug forms, and to methods for using the prodrug forms.

As employed in this application, the term "prodrug" denotes a derivative of allopurinol which derivative, when administered to warm-blooded animals, e.g. humans, is converted into the proven drug, i.e. allopurinol.

The term "transient" indicates that the conversion of the prodrug forms proceeds in such a manner that the proven drug form (parent allopurinol) is released, and the remaining moieties split off remain nontoxic or are metabolized so that nontoxic metabolic products are produced.

These novel prodrug forms of allopurinol are certain derivatives of allopurinol which possess a desirable high lipophilicity and/or improved aqueous solubility in comparison to the parent compound, allopurinol.

2. Description of the Prior Art

Allopurinol is a widely used agent for the treatment and prevention of hyperuricemic states such as gout. Allopurinol and its main metabolite oxipurinol lower the level of uric acid in plasma and urine by inhibiting xanthine oxidase, the enzyme catalyzing the oxidation of hypoxanthine to xanthine and xanthine to uric acid (cf. e.g. Spector, 1977; Elion, 1978). In addition to its use as prophylaxis against and treatment of gout and other chronic hyperuricemic states allopurinol is commonly used to prevent the development of hyperuricosuria that often results from the rapid lysis of cells in patients with malignancies who are undergoing treatment with cytotoxic drugs or radiation (cf. e.g. Elion, 1978).

Allopurinol is conventionally administered orally in the form of tablets. However, the development of nausea and vomiting among patients undergoing cancer chemotherapy frequently precludes the use of oral preparations in these patients. Consequently, a pharmaceutical and medical need exists for allopurinol preparations useful for the control of hyperurecemia in patients with neoplastic disease as well as in other individuals who are unable to take or retain oral medications.

Alternative means of administering allopurinol may be provided by the use of injectable and rectal preparations.

However, since allopurinol is only slightly soluble in water (about 0.5 mg/ml at 25° C.) acceptable injection preparations such as for intramuscular injection, are not available. Presently, it is only possible to deliver sufficient amounts of allopurinol parenterally by infusion. The infusion fluids used contain the sodium salt of allopurinol at a concentration of 0.5–1% and are strongly alkaline (pH about 10.5–11.5); consequently, their administration may cause thrombophlebitis or perivascular inflammation.

With respect to the rectal route of administering allopurinol recent studies have demonstrated that this approach using allopurinol per se is not a suitable and reliable mode of therapy (Chang et al., 1981; Appelbaum et al., 1980, 1982). It was shown in these studies that virtually no allopurinol or only very minute amounts (<5%) is absorbed from various suppository preparations administered rectally to man. This very poor ability of allopurinol to be absorbed rectally can be attributed to the low lipophilicity of the drug combined with its poor water solubility.

Although oral administration of allopurinol provides the attainment of effective serum concentrations the absorption of the compound is not complete. Thus, it has been reported that the absolute systemic bioavailability of oral allopurinol tablets in man are about 70% (Appelbaum et al., 1982) while another study (Elion et al., 1966) reported that about 20–25% of an oral dose is excreted in the stool unchanged. The incomplete and variable absorption behaviour of allopurinol can, like noted above for the rectal absorption, be attributed to the low water and lipid solubility of the drug.

Thus, it is quite obvious that a serious need exists for improved forms of allopurinol, which would be devoid of those disadvantages and drawbacks that to date have characterized the parent drug, allopurinol. From the foregoing, it also appears that successful allopurinol prodrugs for the preparation of pharmaceutically acceptable injection preparations should exhibit a high water-solubility at a physiologically acceptable pH. Furthermore, to provide an efficient, reliable and rapid absorption upon rectal administration it also appears that successful allopurinol prodrugs should possess both a desirable high water-solubility and lipophilicity. In addition to these properties, successful prodrug derivatives should be capable of reverting to the active allopurinol when absorbed into the bloodstream of a warm-blooded animal or when reaching the site of therapeutic activity of the parent drug.

The only previously described prodrug types for allopurinol are some ether derivatives (Hussain & Rytting, 1974), N-Mannich bases (Bundgaard & Johansen, 1981) and N-hydroxymethyl derivatives (Bansal et al., 1981). These compounds differ considerably from the compounds of the present invention. They are extremely unstable in aqueous solutions, are relatively insoluble in water and lipid and apparently offer no advantage over allopurinol with respect to bioavailability following rectal or parenteral administration.

SUMMARY OF THE INVENTION

One object of the present invention is to provide novel prodrug forms of allopurinol, useful for the prevention and treatment of hyperuricemic states such as gout.

Another object of this invention is to provide novel prodrug forms of allopurinol which prodrugs, or transient derivatives, owing to their improved lipid and/or water solubility, exhibit superior bioavailability over allopurinol per se, when administered rectally or orally.

A further object of the present invention is to provide novel transient prodrug forms of allopurinol which are characterized as being highly soluble in water and hence are extremely useful as parenteral delivery forms of allopurinol.

All foregoing objects are obtained with selected transient prodrug forms of allopurinol.

The ring structure named "allopurinol" exists in different tautomeric forms:

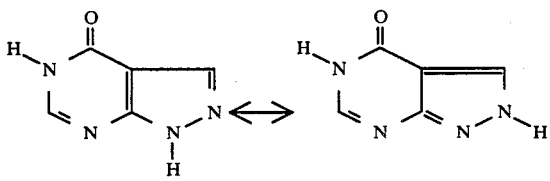

1,5-dihydro-4H—pyrazolo-[3,4-d]pyrimidin-4-one 2,5-dihydro-4H—pyrazolo-[3,4-d]pyrimidin-4-one Two of the tautomeric forms are drawn above and their systemic names are given, but in the present context, the term "allopurinol" encompasses all tautomeric forms of the ring system.

The invention relates to compounds of the formulas Ia or Ib

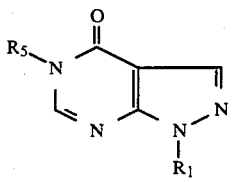

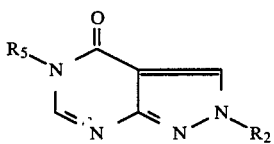

wherein $R_1$ is a group of the formula II

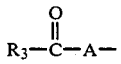

wherein $R_3$ is alkyl; phenyl; phenyl substituted with halogen, lower alkyl, hydroxy, lower alkoxy, acetoxy, or phenoxy; phenyl-lower alkyl in which the phenyl group may be substituted with halogen, lower alkyl, hydroxy, lower alkoxy, acetoxy or phenoxy; or phenyl-lower alkenyl in which the phenyl group may be substituted with halogen, lower alkyl, hydroxy, lower alkoxy, acetoxy, or phenoxy; or $R_3$ is an aromatic 5- or 6-membered heterocyclic ring containing one or two heteroatoms selected from the group consisting of nitrogen, oxygen, and sulfur; and A is a single bond or a group of the formula IIa

wherein the carbon atom is attached to the nitrogen atom of the parent ring system, and wherein $R_6$ and $R_7$ are the same or different and each represent hydrogen or have the same meaning as $R_3$ as defined above; or $R_1$ is a group of the formula III

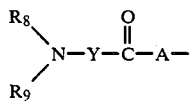

wherein $R_8$ and $R_9$ are the same or different and each represent hydrogen or have the same meaning as $R_3$ as defined above; or $R_8$ and $R_9$ together with the adjacent nitrogen from a 5- or 6-membered heterocyclic ring, which in addition to the nitrogen may contain one or two further heteroatoms selected from the group consisting of nitrogen, oxygen and sulfur; Y is a single bond or a group of the formula IIIa

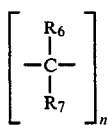

wherein n is an integer from 1 to 5; and A, $R_6$, and $R_7$ are as defined above;
or $R_1$ is a group of the formula IV

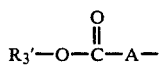

wherein A is as defined above and $R_3'$ has the same meaning as $R_3$ defined above, with the proviso that $R_3$ is not ethyl when A is a bond;
or $R_1$ is a group of the formula VI

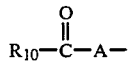

wherein $R_{10}$ is a mono- or polyhalogenated lower alkyl group and A is as defined above;
or $R_1$ is a group of the formula VII

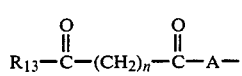

wherein n and A are as defined above, and $R_{13}$ is hydroxy or a group of the formula $-NR_8R_9$ wherein $R_8$ and $R_9$ are as defined above;
or $R_1$ is a group of the formula IX

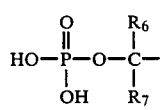

wherein $R_6$ and $R_7$ are as defined above;
$R_2$ is any of the groups II, III, IV, VI, and VII as defined above with the proviso that A solely is the group IIa as defined above;
and $R_5$ is hydrogen or has the same meaning as $R_2$ as defined above,
and salts thereof.

In the present context, the term "alkyl" designates $C_{1-8}$ alkyl which may be straight or branched, such as methyl, ethyl, propyl, isopropyl, butyl, tert.butyl, pentyl, hexyl, heptyl, or octyl. Among the alkyl groups, lower alkyl groups are preferred. The term "lower alkyl" designates $C_{1-4}$ alkyl which may be straight or branched, such as methyl, ethyl, propyl, isopropyl, butyl, or tert.butyl. The term "phenyl-lower alkyl" designates a lower alkyl group (as herein defined) which, in turn, is substituted with a phenyl group. Preferred phenyl-lower alkyl are benzyl, 1- and 2- phenylethyl, 1-, 2-, and 3-phenylpropyl, and 1-methyl-1-phenylethyl The term "lower alkoxy" designates oxy to which a lower alkyl group is attached as defined above; preferred alkoxy groups are methoxy and ethoxy. The term "halogen" designates F, Cl, Br, or I; Cl is preferred. The term "phenyl-lower alkenyl" designates a $C_{2-5}$-monounsaturated aliphatic hydrocarbon group which may be straight or branched, such as propenyl, butenyl or pentenyl, and which in turn is substituted with a phenyl group. Preferred phenyl-lower alkenyl groups are phenyl-substituted propen(2)-yl optionally substituted with methyl or ethyl, such as 3-phenyl-propen(2)-yl (both E and Z forms), 2-methyl-3-phenyl-propen(2)-yl (both E and Z forms), and 3-phenyl-buten(2)-yl (both E and Z forms). Where phenyl groups are substituted with e.g. halogen, lower alkyl, hydroxy, lower alkoxy, acetoxy or phenoxy, they may be mono-, di-, or tri-substituted, and when they are di-, or tri-substituted, the substituents may be the same or different. The term "polyhalogenated lower alkyl" designates lower alkyl (as defined above) substituted with two or more halogen atoms, which may be the same or different. A preferred example of polyhalogenated lower alkyl is trichloromethyl. When, in the formula II, $R_3$ is an aromatic 5- or 6-membered heterocyclic ring containing 1 or 2 hetero atoms selected from the group consisting of nitrogen, oxygen, and sulphur, this may, for instance, be 2-, 3-, or 4-pyridinyl, 2-, or 3-thienyl, 2-, 4-, or 5-thiazolyl, 2-, 4-, or 5-oxazolyl, 2-imidazolyl, 5-isoxazolyl, 5-isothiazolyl, 2-furanyl, 2-, or 5-pyrimidinyl, 5-[1,3]-oxazinyl, or 5-[1,3]-thiazinyl. When, in the formula III, $R_8$ and $R_9$ together with the adjacent nitrogen atom form a 5- or 6-membered heterocyclic ring which in addition to the nitrogen may contain 1 or 2 further hetero atoms selected from the group consisting of nitrogen, oxygen, and sulphur, it may, for instance, be 1-piperidinyl, 1-imidazolyl, 1-pyrazolyl, morpholinyl, 1-piperazinyl, and thiomorpholinyl.

The salts of the compounds of the formulas Ia or Ib include any pharmaceutically acceptable acid addition salt. This term as used herein generally includes the non-toxic acid addition salts of compounds of the formulas Ia or Ib, formed with non-toxic inorganic or organic acids. For example, the salts include salts with inorganic acids, such as hydrochloric, hydrobromic, sulphuric, sulphamic, nitric, phosphoric and the like; and the salts with organic acids such as acetic, propionic, succinic, fumaric, maleic, tartaric, citric, glycolic, stearic, lactic, malic, pamoic, ascorbic, phenylacetic, glutamic, benzoic, salicylic, sulphonic, sulphanilic, and the like.

When one or more asymmetric carbon atoms are present in the side chains, it is understood that the present invention also encompasses all diastereomers or enantiomers, or mixtures thereof. Examples of isomers are D-, L-, and DL-forms.

The compound of formula Ia wherein $R_1$ is ethyloxycarbonyl ($R_1$ is a group of formula IV wherein A is a bond and $R_3'$ is ethyl) and $R_5$ is hydrogen is described in the literature (Bergmann et al, 1979). However, this reference merely teaches a method for preparing this compound and does not disclose or indicate any utility of the compound, nor any properties of the compound that might indicate its utility as a prodrug.

In another aspect the invention relates to pharmaceutical compositions comprising a pharmaceutically acceptable carrier or excipient and a compound of the formulas I'a or Ib

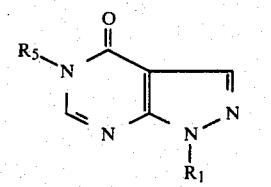

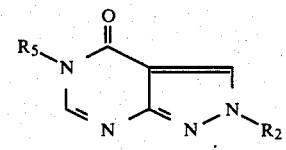

wherein $R_1$ is a group of the formula II

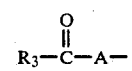

wherein $R_3$ is alkyl; phenyl; phenyl substituted with halogen, lower alkyl, hydroxy, lower alkoxy, acetoxy, or phenoxy; phenyl-lower alkyl in which the phenyl group may be substituted with halogen, lower alkyl, hydroxy, lower alkoxy, acetoxy or phenoxy; or phenyl-lower alkenyl in which the phenyl group may be substituted with halogen, lower alkyl, hydroxy, lower alkoxy, acetoxy, or phenoxy; or $R_3$ is an aromatic 5- or 6-membered heterocyclic ring containing one or two heteroatoms selected from the group consisting of nitrogen, oxygen, and sulfur; and A is a single bond or a group of the formula IIa

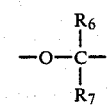

wherein the carbon atom is attached to the nitrogen atom of the parent ring system, and wherein $R_6$ and $R_7$ are the same or different and each represent hydrogen or have the same meaning as $R_3$ as defined above; or $R_1$ is a group of the formula III

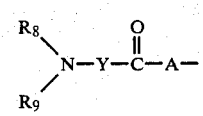

wherein $R_8$ and $R_9$ are the same or different and each represent hydrogen or have the same meaning as $R_3$ as defined above; or $R_8$ and $R_9$ together with the adjacent nitrogen form a 5- or 6-membered heterocyclic ring, which in addition to the nitrogen may contain one or two further heteroatoms selected from the group consisting of nitrogen, oxygen and sulfur; Y is a single bond or a group of the formula IIIa

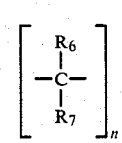

wherein n is an integer from 1 to 5; and A, $R_6$, and $R_7$ are as defined above;

or $R_1$ is a group of the formula IV

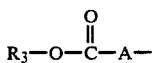 IV wherein $R_3$ and A are as defined above;
or $R_1$ is a group of the formula VI

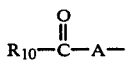 VI wherein $R_{10}$ is a mono- or polyhalogenated lower alkyl group and A is as defined above;
or $R_1$ is a group of the formula VII

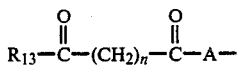 VII wherein n and A are as defined above, and $R_{13}$ is hydroxy or a group of the formula $-NR_8R_9$ wherein $R_8$ and $R_9$ are as defined above;
or $R_1$ is a group of the formula IX

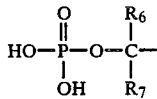 IX wherein $R_6$ and $R_7$ are as defined above;
$R_2$ is any of the groups II, III, IV, VI, and VII as defined above with the proviso that A solely is the group IIa as defined above;
and $R_5$ is hydrogen or has the same meaning as $R_2$ as defined above,
and salts thereof.

In another aspect the present invention also concerns a method for preparing the above mentioned compositions comprising combining a pharmaceutically acceptable carrier or excipient with a compound of the formulas I'a or Ib.

In a further aspect the invention also concerns a method for preparing compounds of the formulas I'a or Ib.

In yet another aspect the invention concerns a method for treating and preventing hyperuricemic states comprising administering an amount effective in lowering the level of uric acid, of a compound of the present invention optionally in a pharmaceutical composition as described above, to warm-blooded animals including humans.

DETAILED DESCRIPTION OF THE INVENTION

As examples of compounds of formula Ia or I'a may be mentioned compounds in which $R_5$ is as defined above, and $R_1$ is one of the following groups ("groups a");

Acetyl
Propionyl
Butyryl
Isobutyryl
Valeryl
Benzoyl
4-Methylbenzoyl
2,4-Dimethylbenzoyl
4-Chlorobenzoyl
4-Methoxybenzoyl
3,4-Dimethoxybenzoyl
4-Hydroxybenzoyl
2-Hydroxylbenzoyl
4-Acetoxybenzoyl
2-Acetoxybenzoyl
4-Phenoxybenzoyl
Phenylacetyl
4-Chlorophenylacetyl
3-Phenylpropionyl
Nicotinoyl
Isonicotinoyl
Picolyl
2-Thienoyl
Cinnamoyl
4-Methylcinnamoyl
4-Chlorocinnamoyl
Glycyl
N,N-Dimethylglycyl
N,N-Diethylglycyl
N,N-Dipropylglycyl
N-Methylglycyl
N-Ethylglycyl
N-Propylglycyl
Alanyl
N,N-Dimethylalanyl
N,N-Diethylalanyl
Leucyl
Norleucyl
Norvalyl
Valyl
Phenylalanyl
3-(N,N-Dimethylamino)propionyl
4-(N,N-Dimethylamino)butyryl
4-(N,N-Diethylamino)butyryl
5-(N,N-Dimethylamino)valeryl
N,N-Dimethylphenylalanyl
Methoxycarbonyl
Ethoxycarbonyl
Butoxycarbonyl
Hexyloxycarbonyl
Phenoxycarbonyl
4-Chlorophenoxycarbonyl
4-Methoxyphenoxycarbonyl
Benzyloxycarbonyl
Carbamoyl
N-Methylcarbamoyl
N-Ethylcarbamoyl
N-Butylcarbamoyl
N-Phenylcarbamoyl
N,N-Dimethylcarbamoyl
Chloroacetyl
Bromoacetyl
Trichloroacetyl
Trifluoroacetyl
2-Chloropropionyl
2-Bromopropionyl
Succinyl
Formyloxymethyl
Acetyloxymethyl
Propionyloxymethyl
Butyryloxymethyl
Isobutyryloxymethyl
Pivaloyloxymethyl
Valeryloxymethyl
Benzoyloxymethyl
4-Chlorobenzoyloxymethyl 4-Methylbenzoyloxymethyl
2,4-Dimethylbenzoyloxymethyl
4-Methoxybenzoyloxymethyl
3,4-Dimethoxybenzoyloxymethyl
4-Hydroxybenzoyloxymethyl
2-Hydroxybenzoyloxymethyl
4-Acetoxybenzoyloxymethyl
2-Acetoxybenzoyloxymethyl
4-Phenoxybenzoyloxymethyl
Phenylacetyloxymethyl
3-Phenylpropionyloxymethyl
Nicotinoyloxymethyl
Isonicotinoyloxymethyl
Picolyloxymethyl
1-(Acetyloxy)ethyl
1-(Acetyloxy)propyl
1-(Butyryloxy)ethyl
1-(Butyryloxy)propyl
(Acetyloxy)(phenyl)methyl
Glycyloxymethyl
N,N-Dimethylglycyloxymethyl
1-(N,N-Dimethylglycyloxy)ethyl
N,N-Diethylglycyloxymethyl
1-(N,N-Diethylglycyloxy)ethyl
N,N-Dipropylglycyloxymethyl
1-(N,N-Dipropylglycyloxy)ethyl
N-Methylglycyloxymethyl
N-Ethylglycyloxymethyl
N-Propylglycyloxymethyl
Alanyloxymethyl
N,N-Dimethylalanyloxymethyl
1-(N,N-Dimethylalanyloxy)ethyl
N,N-Diethylalanyloxymethyl
1-(N,N-Diethylalanyloxy)ethyl
Leucyloxymethyl
N,N-Dimethylleucyloxymethyl
Norleucyloxymethyl
Valyloxymethyl
Norvalyloxymethyl
Phenylglycyloxymethyl
Phenylalanyloxymethyl
N,N-Dimethylphenylalanyloxymethyl
N,N-Diethylphenylalanyloxymethyl
Methoxycarbonyloxymethyl
Ethoxycarbonyloxymethyl
Phenoxycarbonyloxymethyl
Benzyloxycarbonyloxymethyl
Trifluoroacetyloxymethyl
Chloroacetyloxymethyl
Succinyloxymethyl
3-(N,N-Diethylcarbamoyl)propionyloxymethyl
Phosphonooxymethyl
and salts thereof.

Of the compounds in which $R_5$ is different from hydrogen, preferred compounds of the formulas Ia or I'a are compounds in which $R_1$ and $R_5$ are the same, since such compounds are generally easier to prepare.

Among these compounds (i.e. $R_1$ and $R_5$ are the same) more preferred compounds are compounds wherein $R_1$ and $R_5$ are groups of the formulas II or III as defined above, wherein A is a group of formula IIa, and Y is a group of formula IIIa; and salts thereof.

Examples of such compounds are compounds in which $R_1$ and $R_5$ are one of the following groups ("groups b"):
Formyloxymethyl
Acetyloxymethyl
Propionyloxymethyl
Butyryloxymethyl
Isobutyryloxymethyl
Pivaloyloxymethyl
Valeryloxymethyl
Benzoyloxymethyl
4-Chlorobenzoyloxymethyl
2,4-Dimethylbenzoyloxymethyl
4-Methoxybenzoyloxymethyl
3,4-Dimethoxybenzoyloxymethyl
4-Hydroxybenzoyloxymethyl
2-Hydroxybenzoyloxymethyl
4-Acetoxybenzoyloxymethyl
2-Acetyloxybenzoyloxymethyl
4-Phenoxybenzoyloxymethyl
Phenylacetyloxymethyl
3-Phenylpropionyloxymethyl
Nicotinoyloxymethyl
Isonicotinoyloxymethyl
Picolyloxymethyl
1-(Acetyloxy)ethyl
1-(Acetyloxy)propyl
1-(Butyryloxy)ethyl
1-(Butyryloxy)propyl
(Acetyloxy)(phenyl)methyl
Glycyloxymethyl
1-(N,N-Dimethylglycyloxy)ethyl
N,N-Diethylglycyloxymethyl
1-(N,N-Diethylglycyloxy)ethyl
N,N-Dipropylglycyloxymethyl
1-(N,N-Dipropylglycyloxy)ethyl
N-Methylglycyloxymethyl
N-Ethylglycyloxymethyl
N-Propylglycyloxymethyl
Alanyloxymethyl
N,N-Dimethylalanyloxymethyl
1-(N,N-Dimethylalanyloxy)ethyl
N,N-Diethylalanyloxymethyl
1-(N,N-Diethylalanyloxy)ethyl
Leucyloxymethyl
N,N-Dimethylleucyloxymethyl
Norleucyloxymethyl
Valyloxymethyl
Norvalyloxymethyl
Phenylglycyloxymethyl
Phenylalanyloxymethyl
N,N-Dimethylphenylalanyloxymethyl
N,N-Diethylphenylalanyloxymethyl
and salts thereof.

Other more preferred compounds of the formulas Ia or I'a are compounds wherein $R_5$ is hydrogen and $R_1$ is a group of the formula II, III, IV, VI, VII or IX; and salts thereof.

Examples of such compounds are compounds wherein $R_5$ is hydrogen and $R_1$ is a group selected from the groups a specified above.

Among these compounds (i.e. $R_5$ is hydrogen) still more preferred compounds are compounds wherein $R_1$ is a group of the formulas II, III wherein Y is a group of formula IIIa, or VII.

Examples of such compounds are compounds wherein $R_5$ is hydrogen and $R_1$ is one of the following groups ("groups c"):
Acetyl
Propionyl
Butyryl
Isobutyryl
Valeryl
Benzoyl 4-Methylbenzoyl
2,4-Dimethylbenzoyl
4-Chlorobenzoyl
4-Methoxybenzoyl
3,4-Dimethoxybenzoyl
4-Hydroxybenzoyl
2-Hydroxybenzoyl
4-Acetoxybenzoyl
2-Acetoxybenzoyl
4-Phenoxybenzoyl
Phenylacetyl
4-Chlorophenylacetyl
3-Phenylpropionyl
Nicotinoyl
Isonicotinoyl
Picolyl
2-Thienoyl
Cinnamoyl
4-Methylcinnamoyl
4-Chlorocinnamoyl
Glycyl
N,N-Dimethylglycyl
N,N-Diethylglycyl
N,N-Dipropylglycyl
N-Methylglycyl
N-Ethylglycyl
N-Propylglycyl
Alanyl
N,N-Dimethylalanyl
N,N-Diethylalanyl
Leucyl
Norleucyl
Norvalyl
Valyl
Phenylalanyl
3-(N,N-Dimethylamino)propionyl
4-(N,N-Dimethylamino)butyryl
4-(N,N-Diethylamino)butyryl
5-(N,N-Dimethylamino)valeryl
N,N-Dimethylphenylalanyl
Succinyl
Formyloxymethyl
Acetyloxymethyl
Propionyloxymethyl
Butyryloxymethyl
Isobutyryloxymethyl
Pivaloyloxymethyl
Valeryloxymethyl
Benzoyloxymethyl
4-Chlorobenzoyloxymethyl
4-Methylbenzoyloxymethyl
2,4-Dimethylbenzoyloxymethyl
4-Methoxybenzoyloxymethyl
3,4-Dimethoxybenzoyloxymethyl
4-Hydroxybenzoyloxymethyl
2-Hydroxybenzoyloxymethyl
4-Acetoxybenzoyloxymethyl
2-Acetoxybenzoyloxymethyl
4-Phenoxybenzoyloxymethyl
Phenylacetyloxymethyl
3-Phenylpropionyloxymethyl
Nicotinoyloxymethyl
Isonicotinoyloxymethyl
Picolyloxymethyl
1-(Acetyloxy)ethyl
1-(Acetyloxy)propyl
1-(Butyryloxy)ethyl
1-(Butyryloxy)propyl
(Acetyloxy)(phenyl)methyl
Glycyloxymethyl
N,N-Dimethylglycyloxymethyl
1-(N,N-Dimethylglycyloxy)ethyl
N,N-Diethylglycyloxymethyl
1-(N,N-Diethylglycyloxy)ethyl
N,N-Dipropylglycyloxymethyl
1-(N,N-Dipropylglycyloxy)ethyl
N-Methylglycyloxymethyl
N-Ethylglycyloxymethyl
N-Propylglycyloxymethyl
Alanyloxymethyl
N,N-Dimethylalanyloxymethyl
1-(N,N-Dimethylalanyloxy)ethyl
N,N-Diethylalanyloxymethyl
1-(N,N-Diethylalanyloxy)ethyl
Leucyloxymethyl
N,N-Dimethylleucyloxymethyl
Norleucyloxymethyl
Valyloxymethyl
Norvalyloxymethyl
Phenylglycyloxymethyl
Phenylalanyloxymethyl
N,N-Dimethylphenylalanyloxymethyl
N,N-Diethylphenylalanyloxymethyl
Succinyloxymethyl
3-N,N-Diethylcarbamoyl)propionyloxymethyl
and salts thereof.

Still more preferred compounds of the formula Ia are compounds wherein $R_5$ is hydrogen and $R_1$ is a group of the formulas II, III wherein Y is a group of formula IIIa, or VII, wherein A in all the formulas mentioned is a group of formula IIa.

Examples of such compounds are compounds wherein $R_5$ is hydrogen and $R_1$ is one of the groups b specified above.

Even more preferred compounds of the formula Ia are compounds wherein $R_5$ is hydrogen and $R_1$ is a group of the formula III wherein A is a group of formula IIa and Y is a group of formula IIIa.

Examples of such compounds are compounds wherein $R_5$ is hydrogen and $R_1$ is one of the following groups ("groups d"):
Glycyloxymethyl
N,N-Dimethylglycyloxymethyl
1-(N,N-Dimethylglycyloxy)ethyl
N,N-Diethylglycyloxymethyl
1-(N,N-Diethylglycyloxy)ethyl
N,N-Dipropylglycyloxymethyl
1-(N,N-Dipropylglycyloxy)ethyl
N-Methylglycyloxymethyl
N-Ethylglycyloxymethyl
N-Propylglycyloxymethyl
Alanyloxymethyl
N,N-Dimethylalanyloxymethyl
1-(N,N-Dimethylalanyloxy)ethyl
N,N-Diethylalanyloxymethyl
1-(N,N-Diethylalanyloxy)ethyl
Leucyloxymethyl
N,N-Dimethylleucyloxymethyl
Norleucyloxymethyl
Valyloxymethyl
Norvalyloxymethyl
Phenylglycyloxymethyl
Phenylalanyloxymethyl
N,N-Dimethylphenylalanyloxymethyl
N,N-Diethylphenylalanyloxymethyl
and salts thereof.

Particularly preferred compounds of the formula Ia are compounds in which $R_5$ is hydrogen and $R_1$ is N,N-dimethylglycyloxymethyl, N,N-diethylglycyloxymethyl, N,N-dipropylglycyloxymethyl, N,N-dimethylalanyloxymethyl, N,N-diethylalanyloxymethyl, phenylalanyloxymethyl, phenylglycyloxymethyl, or leucyloxymethyl; and salts thereof.

Among the compounds of the formula Ib preferred compounds are compounds in which $R_2$ and $R_5$ are the same. Examples of such compounds are compounds, in which $R_2$ and $R_5$ are groups selected from the groups b specified above.

Even more preferred compounds of the formula Ib are compounds in which $R_2$ and $R_5$ are the same and $R_2$ and $R_5$ are groups of the formula III as defined above wherein A is a group of formula IIa and Y is a group of formula IIIa.

Examples of such compounds are compounds wherein $R_5$ and $R_2$ are the same and are selected from the groups d specified above; and salts thereof.

Other very preferred compounds of the formula Ib are compounds wherein $R_5$ is hydrogen and $R_2$ is a group of the formula II wherein A is a group of formula IIa.

Examples of such compounds are compounds wherein $R_5$ is hydrogen and $R_2$ is one of the following groups ("groups e"):
Formyloxymethyl
Acetyloxymethyl
Propionyloxymethyl
Butyryloxymethyl
Isobutyryloxymethyl
Pivaloyloxymethyl
Valeryloxymethyl
Benzoyloxymethyl
4-Chlorobenzoyloxymethyl
4-Methylbenzoyloxymethyl
2,4-Dimethylbenzoyloxymethyl
4-Methoxybenzoyloxymethyl
3,4-Dimethoxybenzoyloxymethyl
4-Hydroxybenzoyloxymethyl
4-Acetoxybenzoyloxymethyl
4-Phenoxybenzoyloxymethyl
Phenylacetyloxymethyl
3-Phenylpropionyloxymethyl
Nicotinoyloxymethyl
Isonicotinoyloxymethyl
Picolyloxymethyl
1-(Acetyloxy)ethyl
1-(Acetyloxy)propyl
1-(Butyryloxy)ethyl
1-(Butyryloxy)propyl
(Acetyloxy)(phenyl)methyl
and salts thereof.

Specific examples of preferred compounds of formula Ia are:
1-(Acetyloxymethyl)allopurinol
1-(Propionyloxymethyl)allopurinol
1-(Butyryloxymethyl)allopurinol
1-(Glycyloxymethyl)allopurinol
1-(DL-Alanyloxymethyl)allopurinol
1-(L-Alanyloxymethyl)allopurinol
1-(N,N-Dimethylglycyloxymethyl)allopurinol
1-(N,N-Diethylglycyloxymethyl)allopurinol
1-(N,N-Dipropylglycyloxymethyl)allopurinol
1-(DL-N,N-Dimethylalanyloxymethyl)allopurinol
1-(L-N,N-Dimethylalanyloxymethyl)allopurinol
1-(DL-N,N-Diethylalanyloxymethyl)allopurinol
1-(L-N,N-Diethylalanyloxymethyl)allopurinol
1-(DL-Phenylalanyloxymethyl)allopurinol
1-(L-Phenylalanyloxymethyl)allopurinol
1-(DL-Phenylglycyloxymethyl)allopurinol
1-(L-Phenylglycyloxymethyl)allopurinol
1-(DL-Leucyloxymethyl)allopurinol
1-(L-Leucyloxymethyl)allopurinol
1-(DL-Norleucyloxymethyl)allopurinol
1-(L-Norleucyloxymethyl)allopurinol
1-(DL-Norvalyloxymethyl)allopurinol
1-(L-Norvalyloxymethyl)allopurinol
1-(DL-Valyloxymethyl)allopurinol
1-(L-Valyloxymethyl)allopurinol
1-(DL-N,N-Dimethylphenylalanyloxymethyl)allopurinol
1-(DL-N,N-Diethylphenylalanyloxymethyl)allopurinol
and salts thereof.

Specific examples of preferred compounds of formula Ib are:
2-(Acetyloxymethyl)allopurinol
2-(Propionyloxymethyl)allopurinol
2-(Butyryloxymethyl)allopurinol
2-(Benzoyloxymethyl)allopurinol
2,5-bis(Acetyloxymethyl)allopurinol
2,5-bis(Propionyloxymethyl)allopurinol
2,5-bis(Butylryloxymethyl)allopurinol
2,5-bis(Benzoyloxymethyl)allopurinol
2,5-bis(N,N-Dimethylglycyloxymethyl)allopurinol
2,5-bis(N,N-Diethylglycyloxymethyl)allopurinol
2,5-bis(N,N-Dipropylglycyloxymethyl)allopurinol
2,5-bis(DL-N,N-Dimethylalanyloxymethyl)allopurinol
2,5-bis(DL-N,N-Diethylalanyloxymethyl)allopurinol
2,5-bis(DL-Phenylalanyloxymethyl)allopurinol
2,5-bis(L-Phenylalanyloxymethyl)allopurinol
2,5-bis(L-Leucyloxymethyl)allopurinol
and salts thereof.

Specific examples of especially preferred compounds are:
1-(Butyryloxymethyl)allopurinol,
1-(N,N-dimethylglycyloxymethyl)allopurinol,
1-(N,N-diethylglycyloxymethyl)allopurinol,
1-(N,N-dipropylglycyloxymethyl)allopurinol,
1-(DL-N,N-dimethylalanyloxymethyl)allopurinol,
1-(DL-N,N-diethylalanyloxymethyl)allopurinol,
1-(L-phenylalanyloxymethyl)allopurinol,
1-(L-leucyloxymethyl)allopurinol,
1-(L-valyloxymethyl)allopurinol, and
1-(DL-N,N-dimethylphenylalanyloxymethyl)allopurinol,
and salts thereof.

Dose and dosage forms

The compounds of the present invention are conveniently administered to warm-blooded animals, e.g. humans, via rectal, oral or parenteral dosage forms. The dose of the compounds of the present invention administered to warm-blooded animals, e.g. humans, (either as a single dose, a daily dose, or other time-presented doses) will, of course, depend on the requirements of the individual under treatment. The dosage administered, is, therefore, not subject to specific limits. However, the dose of any compound of the formulas I'a or Ib will usually be an amount, which—on a molar basis—is equivalent to the amount of allopurinol necessary to achieve the desired pharmacological or physiological effect. Generally, the single medical dose for warm-blooded animals, which include humans and primates, will be in the range of approximately 25–1000 mg allopurinol equivalents. For humans the daily dose is generally in the range of 300–600 mg allopurinol equivalents regardless of administration form. The daily dose may be administered in 1–3 single doses.

The compounds of the formulas I'a or Ib may be administered in the form of tablets, capsules, suspensions, emulsions, solutions, injectables, suppositories, enemas, various drug delivery devices and in other suitable form. The route of administration may be orally, parenterally or rectally. The formulation and preparation of any of this broad spectrum of dosage forms into which the subject prodrugs can be dispensed is well-known to those skilled in the art of pharmaceutical formulation. Specific information can, however, be found in the text entitled "Remington's Pharmaceutical Sciences", Sixteenth Edition, 1980.

In a typical preparation for oral administration, e.g. tablet or capsule, any one of the compounds of the present invention in a pharmacologically effective amount is combined with any oral nontoxic pharmaceutically acceptable inert carrier such as lactose, starch and microcrystalline cellulose. Additionally, when required, suitable binders (e.g. gelatin), lubricants (e.g. talc or magnesium stearate) and disintegrating agents (e.g. starch or various cellulose derivatives) are included.

Similarly, in a typical formulation for parenteral application (intravenous, intramuscular, subcutaneous or the like), any of the highly water-soluble compounds of the present invention, such as 1-(N,N-dimethylglycyloxymethyl)allopurinol hydrochloride is dissolved in sterile water in a given concentration and sterilized by e.g. membrane filtration, or radiation. The pH of the solution may, if necessary, be adjusted with e.g. hydrochloric acid, sodium hydroxide or a suitable buffer, and a suitable preservative may optionally be added. Similarly, agents like sodium chloride may be added in order to adjust the tonicity of the solution. A suitable parenteral preparation may also consist of the compound formulated as a sterile, solid substance distributed in injection vials. Before dispensing, water for injection is added to dissolve the compound.

For the rectal application of the allopurinol prodrugs of this invention, typical dosage forms include suppositories (emulsion and suspension types), rectal gelatin capsules (solutions and suspensions), and enemas or micro-enemas (solutions and suspensions). Thus, in a typical suppository formulation, any one of the compounds of this invention is combined with any pharmaceutically acceptable suppository base such as cocoa butter, esterified fatty acids ($C_{10}$–$C_{18}$), glycerinated gelatin, and various water-soluble or dispersible bases like polyethylene glycols and polyoxyethylene sorbitan fatty acid esters. Various additives like salicylates or surfactant materials may be incorporated. Enemas or micro-enemas of the solution type may simply be prepared by dissolving the water-soluble prodrugs of this invention in water or in water containing e.g. 0.5% of methylcellulose or another viscosity-increasing agent.

The novel and useful allopurinol prodrugs of the invention are also adaptable for administration to warm-blooded animals from various novel drug delivery systems such as gastrointestinal drug delivery devices and rectally applied osmotic delivery devices, wherein the delivery device is manufactured from naturally occurring or synthetic polymeric materials. Specific information about osmotic delivery systems for rectal application can be found in De Leede & De Boer (1981) and De Leede et al. (1982).

From the foregoing description, it is obvious that due to the much improved water-solubility of selected members of the claimed prodrugs over allopurinol per se and derivatives of the prior art, superior parenteral formulation and administration is achieved. Similarly, an exceptionally improved rectal bioavailability is achieved owing to the increased water-solubility and/or lipophilicity of the subject compounds.

The compounds of the present invention may be prepared by various methods.

One method (a) for preparing compounds of the formula I'a wherein $R_5$ is hydrogen and A is a bond comprises reacting allopurinol with a compound of the formula XI

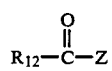

$$R_{12}-\overset{\overset{O}{\|}}{C}-Z \qquad \text{XI}$$

wherein $R_{12}$ has the same meaning as $R_3$ as defined above; $R_{12}$ is a group of the formula III'

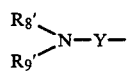

$$\begin{array}{c} R_8' \\ R_9' \end{array}\!\!\!\!>\!\!N-Y- \qquad \text{III'}$$

wherein Y is as defined above, and $R_8'$ and $R_9'$ have the same meaning as $R_8$ and $R_9$ as defined above; or $R_8'$ or $R_9'$ are an amino protecting group;

$R_{12}$ is a group of the formula IV'

$$R_3-O- \qquad \text{IV'}$$

wherein $R_3$ is as defined above;
$R_{12}$ has the same meaning as $R_{10}$ as defined above;
or $R_{12}$ is a group of the formula VII'

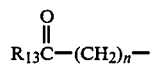

$$R_{13}\overset{\overset{O}{\|}}{C}-(CH_2)_n- \qquad \text{VII'}$$

wherein n is as defined above, and $R_{13}$ is hydroxy or a group of the formula $-NR_8R_9$ wherein $R_8$ and $R_9$ are as defined above; and Z is a leaving group; and then, if an amino protecting group has been used, removing the protecting group.

Another method (b) for preparing compounds of the formula I'a wherein $R_5$ is hydrogen or compounds of formula Ib wherein $R_2$ and $R_5$ are the same, and wherein A is $-CH_2-$, comprises reacting 1-hydroxymethylallopurinol or 2,5-dihydroxymethylallopurinol with a compound of the formula XI as shown above and wherein $R_{12}$ is as defined above; and then, if an amino protecting group has been used, removing the protecting group.

A method (c) for preparing compounds of formulas I'a or Ib wherein either $R_5$ is hydrogen or $R_1$ and $R_5$ are the same or $R_2$ and $R_5$ are the same, comprises reacting allopurinol with a compound of the formula XII

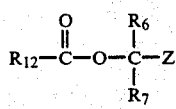

XII wherein $R_6$, $R_7$, $R_{12}$ and Z are as defined above, and then, if an amino protecting group has been used, removing the protecting group.

Other methods (d) and (e) for preparing compounds of the formula I'a wherein $R_5$ is different from hydrogen are contemplated.

Method (d) comprises
reacting a compound of the formula XIII

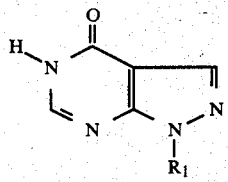

XIII wherein $R_1$ is as defined above in connection with formula I'a, with a compound of the formula XII, wherein $R_6$, $R_7$, $R_{12}$, and Z are as defined; and then, if an amino protecting group has been used, removing the protecting group.

Method (e) comprises
reacting a compound of the formula XIV

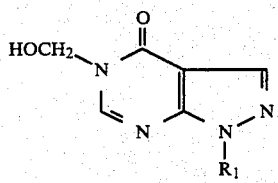

XIV wherein $R_1$ is as defined above in connection with formula I'a with a compound of the formula XI as shown above, wherein $R_{12}$ and Z are as defined above; and then, if an amino protecting group has been used, removing the protecting group.

A method (f) for preparing compounds of the formula Ib wherein $R_5$ is different from hydrogen is contemplated.

Method (f) comprises
reacting a compound of the formula XV

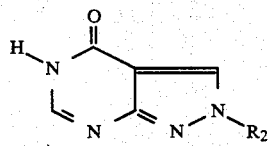

XV wherein $R_2$ is as defined above, with a compound of the formula XII, wherein $R_6$, $R_7$, $R_{12}$, and Z are as defined above; and then, if an amino protecting group has been used, removing the protecting group.

Another method (g) for preparing compounds of the formula I'a wherein $R_5$ is hydrogen or compounds of formula Ib wherein $R_2$ and $R_5$ are the same comprises reacting allopurinol, 1-hydroxymethylallopurinol, or 2,5-dihydroxymethylallopurinol with a compound of the formula V'''

V''' wherein $R_3$ is as defined above.

Still another method (h) for preparing compounds of the formula I'a wherein $R_5$ is hydrogen or compounds of formula Ib wherein $R_2$ and $R_5$ are the same comprises reacting allopurinol, 1-hydroxymethylallopurinol, or 2,5-dihydroxymethylallopurinol with a compound of the formula VII''

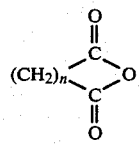

VII'' wherein n is as defined above.

A method (i) for preparing compounds of the formula I'a wherein $R_5$ is hydrogen or compounds of formula Ib wherein $R_2$ and $R_5$ are the same comprises reacting a compound of the formula XVI

XVI wherein $R_8$ and $R_9$ are as defined above, with a compound of formula XVII

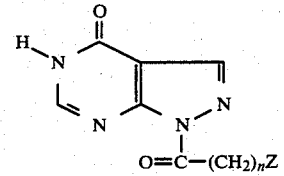

XVII or with a compound of formula XVIII

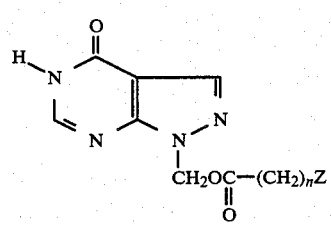

XVIII or with a compound of formula XIX

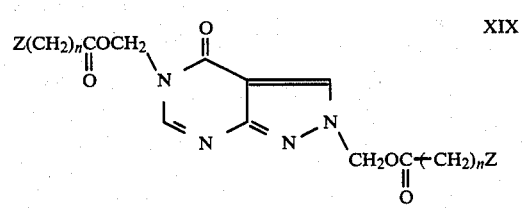

XIX wherein n and Z are as defined above.

A method (j) for preparing compounds of the formula I'a wherein $R_1$ is

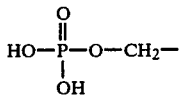

and R$_5$ is hydrogen is contemplated.

Method (j) comprises (1) hydrogenation of the corresponding dibenzyl phosphate, or (2) hydrolysis of the corresponding 2-cyanoethyl phosphate, or (3) reacting 1-hydroxymethylallopurinol with pyrophosphoryl tetrachloride followed by hydrolysis.

In the present context the name 1-hydroxymethylallopurinol designates the compound 1-(hydroxymethyl)-1,5-dihydro-4H-pyrazolo[3,4-d]pyrimidin-4-one and tautomeric forms hereof, and the name 2,5-dihydroxymethylallopurinol designates 2,5-[bis(hydroxymethyl)]-1,5-dihydro-4H-pyrazolo[3,4-d]pyrimidin-4-one and tautomeric forms hereof. The synthesis of both compounds have been described (Bansal et al (1981)). It is noted that in this reference, the compound which in the present context is designated 2,5[bis(hydroxymethyl)]-1,5-dihydro-4H-pyrazolo[3,4-d]pyrimidin-4-one in the cited reference is designated as the corresponding 1,5-[bis(hydroxymethyl)]-1,5-dihydro-4H-pyrazolo[3,4-d]pyrimidin-4-one. However, according to analyses performed by the present applicants, the compound prepared according to the teaching of the reference is believed in fact to be the 2,5-compound, for which reason the compound has been designated as the 2,5-compound above. However, as it can still not be concluded with certainty that the compound is indeed the 2,5-compound, the above designation should be understood as covering alternatively the 1,5-compound provided the synthesis described in the reference is in fact conclusively found to result in the 1,5-compound.

The assignment of the actual positions of the substituents is based on the UV and NMR spectra according to the principles set forth in Bergman et al (1979).

As examples of leaving groups Z may be mentioned chlorine, bromine and iodine. Group Z may also be an acyloxy group, i.e. the reacting compound of e.g. formula XI may be an anhydride or a mixed anhydride. When Z is hydroxy a dehydrating agent (e.g. a carbodiimide) has to be present and normally, a sulfonic acid is added to suppress side-reactions.

The term "amino protecting group" designates groups readily removable by hydrolysis or hydrogenation. As examples of such amino protecting groups may be mentioned methyloxycarbonyl, ethyloxycarbonyl, tert.butyloxycarbonyl, benzyloxycarbonyl, formyl, acetyl, trityl, or the like.

Methods (a), (b) and (e) are performed under essentially the same conditions. The reaction is carried out without a solvent or in a solvent (e.g. pyridine, N,N-dimethylformamide, dimethyl sulfoxide, methylene chloride, or the like). Usually a base (e.g. a tertiary amine, pyridine, potassium carbonate, or the like) has to be present. The temperature during the reaction is usually between 0° C. and the boiling point of either the solvent or the boiling point of one of the reactants. The reaction time is normally from 1 to 96 hours.

Methods (c), (d) and (f) are performed under the same conditions. The leaving group Z will often be chlorine, bromine or iodine. The reaction is carried out preferably in a polar solvent (e.g. acetone, N,N-dimethylformamide, dimethylsulfoxide, or the like) and in the presence of a base (a metal carbonate, a tertiary amine, or the like). The reaction temperature will normally be between 0° C. and 100° C. and the reaction time from 1 to 96 hours. In method (c) a mixture of compounds are normally obtained. Dependent on the reaction conditions and on the number of equivalents of the compound of the formula XII used as reagent, compounds with a substituent R$_2$ alone (i.e. R$_5$ is hydrogen) and compounds in which R$_2$ and R$_5$ are the same, are obtained. As by-products, compounds with a substituent R$_1$ alone and compounds in which R$_1$ and R$_5$ are the same are also obtained. The mixture of compounds can be separated by manners known per se, i.e. crystallization or column chromatography.

Method (g) is performed in an inert solvent (e.g. toluene, methylene chloride, N,N-dimethylformamide, or the like). The reaction is carried out at a temperature from 0° C. to the boiling point of the solvent, and for a period of time from 1 to 96 hours.

Method (h) is normally performed in a solvent (e.g. pyridine, N,N-dimethylformamide, or the like.) The reaction temperature is preferably from 0° C. to 150° C. and the reaction time from 1 hour to 96 hours.

Method (i) is normally performed in a solvent such as an alcohol (e.g. methanol or ethanol), acetone, dimethylsulfoxide, N,N-dimethylformamide, pyridine or the like in the presence of a base (e.g. an alkali metal carbonate or a tertiary amine) or in an excess of the compound of formula XVI at a temperature from −20° C. to the boiling point of the solvent.

Key: (Δ), 2,5-bis(Butyryloxymethyl)allopurinol; (o) 1-(N,N-diethylglycyloxymethyl)allopurinol; and (•), 1-(acetyl(allopurinol.

Figure 3:
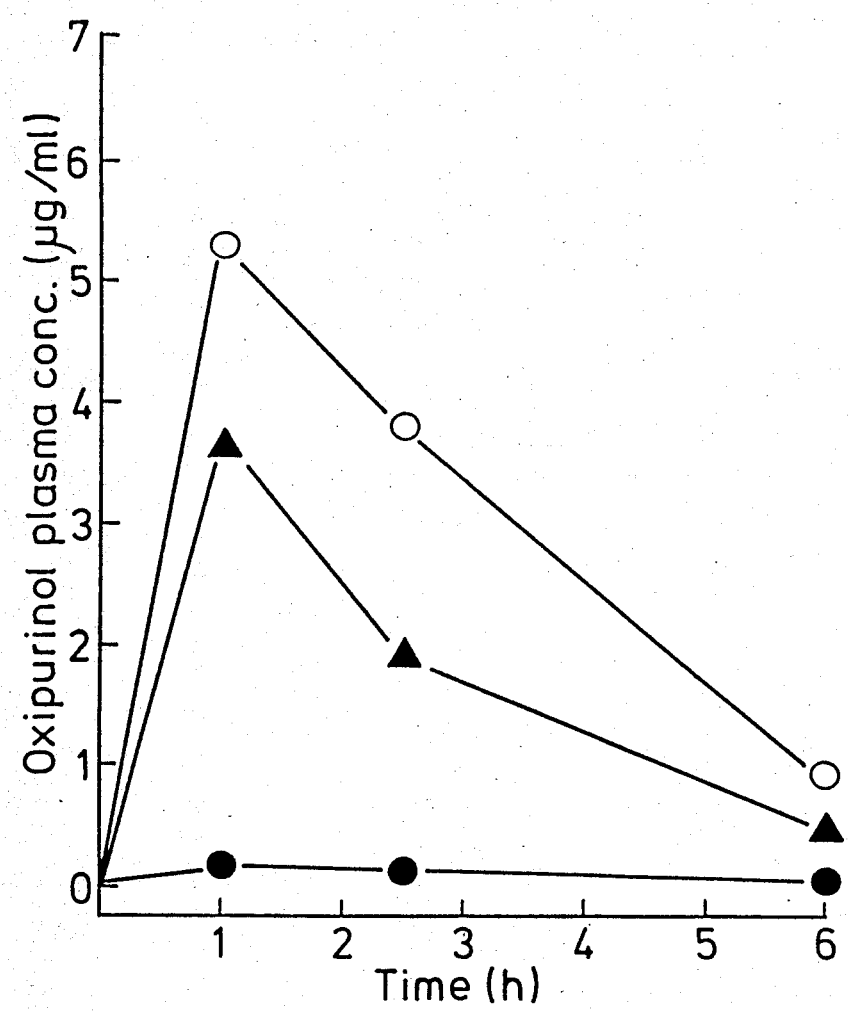

FIG. 3 shows mean plasma levels of oxipurinol versus time plots obtained after rectal administration of suppositories of allopurinol (•), 1-(butryloxymethyl)allopurinol (Δ) and 1-(N,N-diethylglycyloxymethyl)allopurinol hydrochloride (o) to rabbits at a dose of 25 mg allopurinol equivalents (cross-over study involving rabbits each weighing 2.7 kg). The plasma levels of allopurinol were below 1 μg/ml at all of the three blood sampling times.

Figure 4:
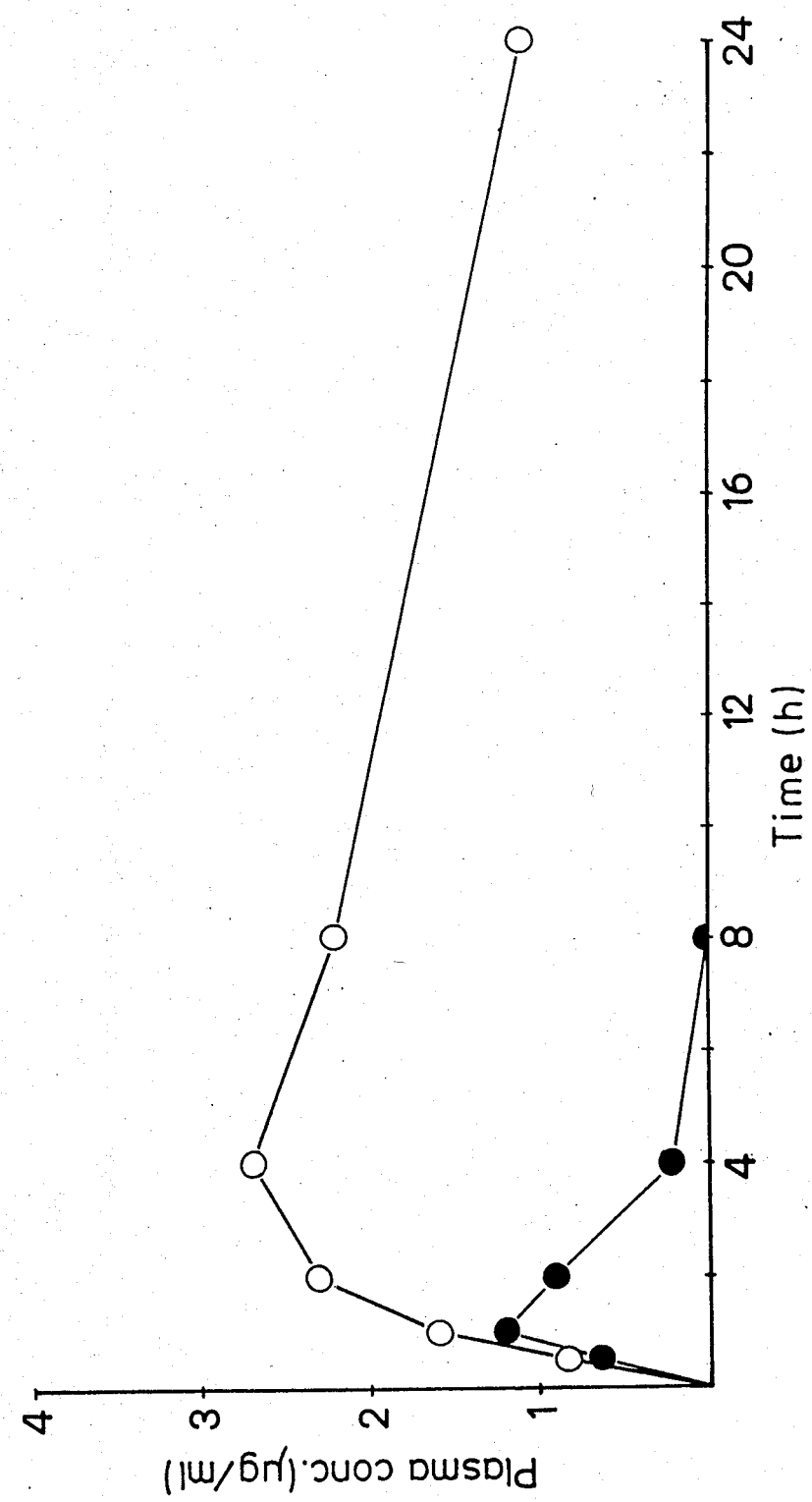

FIG. 4 shows mean plasma levels of oxipurinol (o) and allopurinol (•) versus time plots obtained after rectal administration of suppositories of 1-(N,N-diethylglycyloxymethyl)allopurinol hydrochloride to five human volunteers at a dose of 350 mg allopurinol equivalents.

Figure 5:
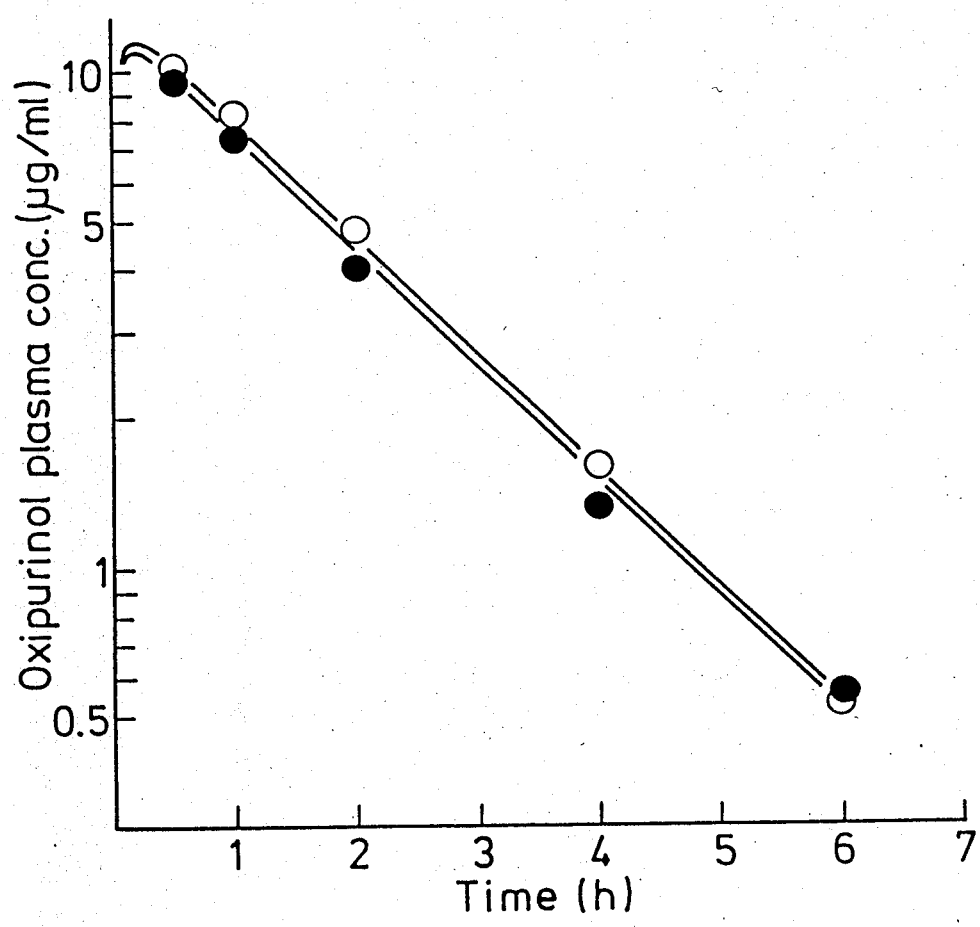

FIG. 5 shows mean plasma levels of oxipurinol versus time plots after intravenous administration of allopurinol (o) and 1-(N,N-diethylglycyloxymethyl)allopurinol hydrochloride (•) to four rabbits at a dose of 25 mg allopurinol equivalents. The plasma levels of allopurinol were below 1 μg/ml at all blood sampling times.

The present invention is further illustrated by the following examples which, however, are not to be construed as limiting. The examples especially illustrate the preferred embodiments of the invention.

Spectral and chromatographical data of the prepared compounds are given in Table 1.

EXAMPLE 1

1-(Acetyl)allopurinol

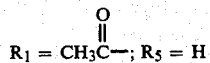

[Method (a)]

$R_1 = CH_3C(O)-$; $R_5 = H$

A suspension of allopurinol (500 mg, 3.67 mmole) in acetic acid anhydride (8 ml) was heated in an oil bath at 130° C. for five hours. After cooling, water (10 ml) was added and the mixture was stirred at room temperature for three hours. The precipitate was collected and washed with water and dried, yielding 375 mg (57%). Recrystallization from ethanol-N,N-dimethylformamide gave an analytically pure compound, m.p. 251°–254° C. (dec.).

EXAMPLE 2

1-(Propionyl)allopurinol

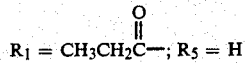

[Method (a)]

$R_1 = CH_3CH_2C(O)-$; $R_5 = H$

The compound was prepared from allopurinol and propionic acid anhydride by the procedure described in Example 1. The yield was 60%. Recrystallization from ethanol-N,N-dimethylformamide gave an analytically pure product, m.p. 259°–263° C.

EXAMPLE 3

1-(Butyryl)allopurinol

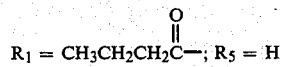

[Method (a)]

$R_1 = CH_3CH_2CH_2C(O)-$; $R_5 = H$

The compound was prepared from allopurinol and butyric acid anhydride by the procedure described in Example 1. The yield was 52%. Recrystallization from ethanol gave an analytically pure product, m.p. 222°–225° C.

EXAMPLE 4

1-(Chloroacetyl)allopurinol

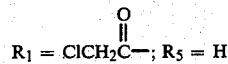

[Method (a)]

$R_1 = ClCH_2C(O)-$; $R_5 = H$

A mixture of allopurinol (2.7 g; 20 mmole) and chloroacetic acid anhydride (6.8 g; 40 mmole) in N,N-dimethylformamide (20 ml) was heated to 80° C. and a clear solution was obtained. After 1 hour, the solution was cooled and the precipitate was collected and washed with acetone. Yield: 2.6 g (61%), m.p. 233°–236° C. (dec.).

EXAMPLE 5

1-(Benzoyl)allopurinol

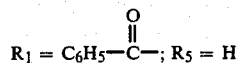

[Method (a)]

$R_1 = C_6H_5C(O)-$; $R_5 = H$

The compound was prepared from allopurinol and benzoic acid anhydride by the procedure described in Example 4. The yield was 50%. Recrystallization from N,N-dimethylformamide gave an analytically pure compound, m.p. 270°–273° C. (dec.).

EXAMPLE 6

1-(Acetyloxymethyl)allopurinol

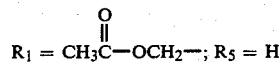

[Method (b)]

$R_1 = CH_3C(O)-OCH_2-$; $R_5 = H$

A mixture of 1-hydroxymethylallopurinol (1.6 g; 10 mmole) and acetic acid anhydride (2.5 ml) in pyridine (10 ml) was stirred at room temperature for 20 hours. The precipitate was collected, washed with ethanol, and dried. Yield: 780 mg (47%), m.p. 257° C.

EXAMPLE 7

1-(Benzoyloxymethyl)allopurinol

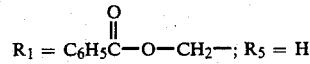

[Method (b)]

$R_1 = C_6H_5C(O)-O-CH_2-$; $R_5 = H$

A mixture of 1-hydroxymethylallopurinol (0.8 g; 5 mmole) and benzoyl chloride (0.75 ml; 6.5 mmole) in pyridine (10 ml) was stirred at room temperature for 3 hours. Water (30 ml) was added and after standing for 20 hours at 5° C., the precipitate was collected and recrystallized from ethanol. Yield: 900 mg (67%), m.p. 217°–219° C.

EXAMPLE 8

1-(Nicotinoyloxymethyl)allopurinol

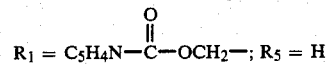

[Method (b)]

$R_1 = C_5H_4N-C(O)-OCH_2-$; $R_5 = H$

The compound was prepared from 1-hydroxymethylallopurinol and nicotinoylchloride by essentially the same procedure as described in Example 7. After recrystallizaion from ethanol, the yield was 30%, m.p. 242°–243° C.

EXAMPLE 9

1-(Chloroacetyloxymethyl)allopurinol

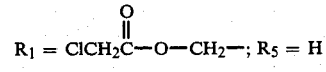

[Method (b)]

$R_1 = ClCH_2C(O)-O-CH_2-$; $R_5 = H$

A mixture of 1-hydroxymethylallopurinol (0.83 g; 5 mmole) and chloroacetic acid anhydride (1.03 g; 6 mmole) in pyridine (20 ml) was stirred at room temperature for 18 hours. Ethanol (20 ml) was added and the precipitate collected, and recrystallized from ethanol. M.p. 203°–205° C. (dec.).

EXAMPLE 10

1-(Butyryloxymethyl)allopurinol

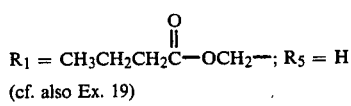 [Method (b)]

$R_1 = CH_3CH_2CH_2\overset{O}{\underset{\|}{C}}-OCH_2-$; $R_5 = H$ (cf. also Ex. 19)

To a suspension of 1-hydroxymethylallopurinol (1.44 g; 8.7 mmole) in methylene chloride (100 ml) was added triethylamine (2.64 g; 26 mmole) and butyrylchloride (2.20 g; 20.8 mmole). The mixture was stirred at room temperature for twenty hours. The resulting clear solution was washed with water (50 ml), aqueous sodium hydrogen-carbonate (2.5%, 50 ml), and water (2×50 ml). The solution was dried and evaporated. The residue was triturated with ethyl acetate yielding 567 mg (28%) of crude product. Recrystallization from ethanol yielded an analytically pure compound, m.p. 224°–226° C.

EXAMPLE 11

1-(N,N-Dimethylglycyloxymethyl)allopurinol (hydrochloride)

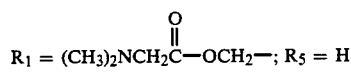 [Method (b)]

$R_1 = (CH_3)_2NCH_2\overset{O}{\underset{\|}{C}}-OCH_2-$; $R_5 = H$

A mixture of 1-hydroxymethylallopurinol (2.0 g; 12 mmole), N,N-dimethylglycine (1.25 g; 12 mmole), N,N′-dicyclohexylcarbodiimide (2.5 g; 12 mmole), and 4-toluenesulfonic acid (150 mg) in pyridine (40 ml) was stirred at room temperature for 48 hours. Methylene chloride (80 ml) was added. The mixture was filtered and the filtrate was evaporated in vacuo. The residue was extracted with two 50 ml portions of boiling methylene chloride, and the extracts were evaporated. The residue was recrystallized from ethyl acetate. The crude compound obtained was suspended in ethanol (20 ml) and a 2N solution of hydrochloric acid in ethyl acetate (8 ml) was added followed by ethylacetate (20 ml). The precipitate was collected (1.32 g) and recrystallized from methanol-ether yielding an analytically pure product, m.p. 203°–206° C. (dec.).

EXAMPLE 12

1-[4-(N,N-Dimethylamino)butyryloxymethyl]allopurinol (hydrochloride)

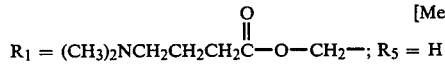 [Method (b)]

$R_1 = (CH_3)_2NCH_2CH_2CH_2\overset{O}{\underset{\|}{C}}-O-CH_2-$; $R_5 = H$

Using the same procedure as described in Example 11, but using N,N-dimethyl-4-aminobutyric acid instead of N,N-dimethylglycine yielded the title compound, m.p. 150°–155° C. (dec.).

EXAMPLE 13

1-(DL-N,N-Diethylalanyloxymethyl)allopurinol (hydrochloride)

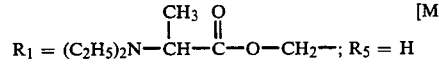 [Method (b)]

$R_1 = (C_2H_5)_2N-\underset{\underset{CH_3}{|}}{CH}-\overset{O}{\underset{\|}{C}}-O-CH_2-$; $R_5 = H$ The compound was prepared from 1-hydroxymethylallopurinol and DL-N,N-diethylalanine by the procedure described in Example 11. The yield was 24%, m.p. 165°–170° C. (dec.).

EXAMPLE 14

1-(N,N-Dipropylglycyloxymethyl)allopurinol (hydrochloride)

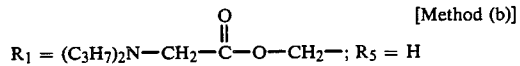 [Method (b)]

$R_1 = (C_3H_7)_2N-CH_2-\overset{O}{\underset{\|}{C}}-O-CH_2-$; $R_5 = H$

The compound was prepared from 1-hydroxymethylallopurinol and N,N-dipropylglycine by the procedure described in Example 11. The compound crystallized from ethanol 195°–198° C. (dec.).

EXAMPLE 15

1-(N,N-Diethylglycyloxymethyl)allopurinol (hydrochloride)

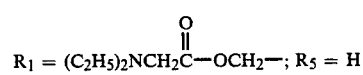 [Method (b)]

$R_1 = (C_2H_5)_2NCH_2\overset{O}{\underset{\|}{C}}-OCH_2-$; $R_5 = H$

A mixture of 1-hydroxymethylallopurinol (3.8 g; 16.8 mmole), N,N-diethylglycine hydrochloride (2.88 g; 17 mmole), N,N′-dicyclohexylcarbodiimide (3.6 g; 17.5 mmole), and 4-toluenesulfonic acid (270 mg) in pyridine (60 ml) was stirred at room temperature for 24 hours. Methylene chloride (50 ml) was added to the reaction mixture. The precipitate was collected and stirred with water (15 ml). The insoluble compound was filtered off and washed with water and the combined filtrates were evaporated in vacuo. The residue was recrystallized twice from methanol-ether yielding an analytically pure compound (1.3 g; 25%), m.p. 196°–198° C. (dec.).

EXAMPLE 16

1-(DL-Alanyloxymethyl)allopurinol (hydrobromide)

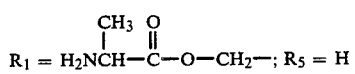 [Method (b)]

$R_1 = H_2NCH-\underset{\underset{CH_3}{|}}{C}-\overset{O}{\underset{\|}{}}-O-CH_2-$; $R_5 = H$ A mixture of 1-hydroxymethylallopurinol (1.6 g; 10 mmole), N-benzyloxycarbonyl-D,L-alanine (2.23 g; 10 mmole), N,N′-dicyclohexylcarbodiimide (2.06 g; 10 mmole), and 4-toluenesulfonic acid (150 mg) in pyridine (60 ml) was stirred at room temperature for 20 hours. Methylene chloride (100 ml) was added and the mixture was filtered. The filtrate was evaporated in vacuo and the residue was extracted with boiling methylene chloride (3×50 ml). The methylene chloride was evaporated and the residue was recrystallized from ethyl acetate-ethanol. To the crude N-protected compound was added a 33% solution of hydrobromic acid in acetic acid (8 ml). The mixture was stirred at room temperature for seven minutes and ethyl acetate (50 ml) was added. The precipitate (520 mg, 16%) was collected and recrystallized from methanol. The title compound was crystallized with ⅔ mole of water, m.p. 195°–198° C. (dec.).

EXAMPLE 17

1-(Succinyloxymethyl)allopurinol

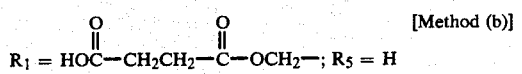
$R_1 = HOC-CH_2CH_2-C-OCH_2-; \quad R_5 = H$ [Method (b)]

A mixture of 1-hydroxymethylallopurinol (1.6 g; 10 mmole) and succinic acid anhydride in pyridine (20 ml) was stirred at room temperature for 96 hours. Hydrochloric acid 4N (50 ml) was added and the precipitate was collected. From ethanol-N,N-dimethylformamide the title compound crystallized with 0.25 equivalent of water. M.p. 217°–219° C. (dec.).

EXAMPLE 18

(1) $R_1=R_5=$tert.butyloxymethyl [Method (c)]
(2) $R_2=R_5=$tert.butyloxymethyl
(3) $R_1=$tert.butyloxymethyl; $R_5=$hydrogen
(4) $R_2=$tert.butyloxymethyl; $R_5=$hydrogen To a solution of allopurinol (2.04 g; 15 mmole) in dimethyl sulfoxide (45 ml) kept at 40° C. were added potassium carbonate (2.07 g; 15 mmole) and then dropwise during one hour a solution of chloromethyl pivalate (2.2 g; 15 mmole) in dimethyl sulfoxide (15 ml). The mixture was stirred at 40° C. for four hours and poured on ice (75 g). After acidification, the mixture was extracted with chloroform (3×70 ml). The extracts were washed with water, dried, and evaporated. Toluene (5 ml) was added to the residue, and the solid compound formed was collected by filtration and washed on the filter with ether (2×5 ml). Recrystallization of the solid from ethyl acetate gave analytically pure 2-(pivaloyloxymethyl)allopurinol (813 mg; m.p. 180°–181° C.).

The toluene-ether filtrate from the crude solid was evaporated in vacuo. Column chromatography (CC) (silica gel, eluents toluene-ethyl acetate-methanol) was performed on the residue, and the compounds were collected in the following order:
(1) 1,5-bis(Pivaloyloxymethyl)allopurinol (90 mg; m.p. 136°–137° C., recrystallized from ether-light petroleum).
(2) 2,5-bis(Pivaloyloxymethyl)allopurinol (402 mg; m.p. 145°–146° C., recrystallized from ethyl acetate-ether-light petroleum).
(3) 1-(Pivaloyloxymethyl)allopurinol (151 mg; m.p. 185°–187° C., recrystallized from ethyl acetate).

EXAMPLE 19

(1) $R_1=R_5=$butyloxymethyl [Method (c)]
(2) $R_2=R_5=$butyloxymethyl
(3) $R_1=$butyloxymethyl; $R_5=$hydrogen
(4) $R_2=$butyloxymethyl; $R_5=$hydrogen By using the same procedure as described in Example 18 and equivalent amounts of allopurinol and chloromethyl butyrate, the following compounds were obtained:
(1) 1,5-bis(Butyryloxymethyl)allopurinol, m.p. 122°–123° C. (from ethyl acetate-ether-light petroleum).
(2) 2,5-bis(Butyryloxymethyl)allopurinol, m.p. 133°–135° C. (from ethyl acetate-ether-light petroleum).
(3) 1-(Butyryloxymethyl)allopurinol, m.p. 220°–225° C. (from ethyl acetate).
(4) 2-(Butyryloxymethyl)allopurinol, m.p. 182°–183° C. (from ethyl acetate).

EXAMPLE 20

1-(N,N-Dimethylglycyl)allopurinol (hydrochloride)

$R_1=(CH_3)_2NCH_2CO-; \quad R_5=H$ [Method (a)]

To a suspension of allopurinol (778 mg, 5.7 mmole) in 5 ml of N,N-dimethylformamide was added a solution of N,N-dimethylglycinyl chloride hydrochloride (5.7 mmole) in 10 ml of N,N-dimethylformamide. The mixture was heated to 80° C. for 1 hour. After cooling the precipitate was collected and washed with ethanol. Yield: 209 mg, m.p. 192°–196° C. (dec.).

EXAMPLE 21

1-(Ethoxycarbonyloxymethyl)allopurinol $R_1=CH_3CH_2-O-CO-O-CH_2-; \quad R_5=H$ [Method (b)]

The compound was prepared from 1-hydroxymethylallopurinol and ethyl chloroformate by the same procedure as described in Example 7. After recrystallization from ethanol the yield was 38%, m.p. 228° C.

EXAMPLE 22

1-(DL-Phenylglycyloxymethyl)allopurinol (hydrobromide)

$R_1=C_6H_5CH(NH_2)CO-OCH_2-; \quad R_5=H$ [Method (b)]

The compound was prepared from 1-hydroxymethylallopurinol and N-(benzyloxycarbonyl)-DL-phenylglycine by the procedure described in Example 16. The analytically pure title compound crystallized from methanol-ether, m.p. 192°–195° C. (dec.).

EXAMPLE 23

2,5-bis(Butyryloxymethyl)allopurinol

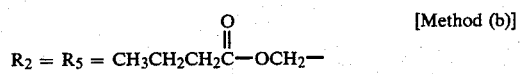
$R_2 = R_5 = CH_3CH_2CH_2C-OCH_2-$ [Method (b)]

A mixture of 400 mg of 2,5-dihydroxymethylallopurinol (prepared as described by Bansal et al. (1981), where the compound is designated 1,5-[bis(hydroxymethyl)]-1,5-dihydro-4H-pyrazolo[3,4-d]pyrimidin-4-one), butyric acid anhydride (1 ml), and pyridine (5 ml) was stirred at room temperature for 24 hours. Water (20 ml) was added to the solution and after stirring for 2 hours the precipitate was collected. Recrystallization from ethyl acetate afforded 268 mg of the title compound, which had the same m.p. and spectral data as the compound synthesized according to Example 19.

EXAMPLE 24

2,5-bis(Acetoxymethyl)allopurinol

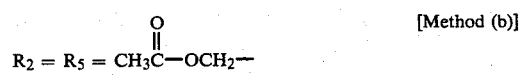
$R_2 = R_5 = CH_3C-OCH_2-$ [Method (b)]

The compound was prepared from 2,5-dihydroxymethylallopurinol and acetic acid anhydride by the procedure described in Example 23. Recrystallization from ethanol gave an analytically pure product in a yield of 68%, m.p. 153°–154° C.

EXAMPLE 25

2,5-bis-(DL-Alanyloxymethyl)allopurinol (dihydrobromide)

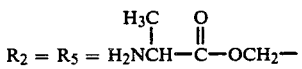 [Method (b)]

$R_2 = R_5 = H_2NCH\text{—}C\text{—}OCH_2\text{—}$ (with H₃C on the CH and C=O)

The compound was prepared from 2,5-dihydroxymethylallopurinol and the double amounts of N-(benzyloxycarbonyl)-D,L-alanine, N,N'-dicyclohexylcarbodiimide, and pyridine by essentially the same procedure as described in Example 16. Recrystallization from methanol-ethyl acetate-ether yielded 16% of the title compound, m.p. 190°–192° C. (dec.). The compound crystallized with 0.5 mole of methanol.

EXAMPLE 26

1-[4-(N,N-Dimethylamino)butyryl]allopurinol (hydrochloride)

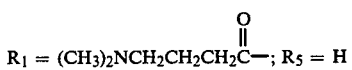 [Method (a)]

$R_1 = (CH_3)_2NCH_2CH_2CH_2C\text{—}$; $R_5 = H$

The compound was prepared from allopurinol and 4-(N,N-dimethyl)butyryl chloride hydrochloride by the same procedure as described in Example 20. The compound crystallized with ½ mole of water and did not melt below 270° C.

EXAMPLE 27

1-(DL-Phenylalanyloxymethyl)allopurinol (hydrobromide)

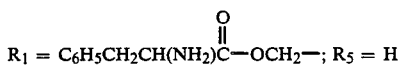 [Method (b)]

$R_1 = C_6H_5CH_2CH(NH_2)C\text{—}OCH_2\text{—}$; $R_5 = H$

The compound was prepared from 1-hydroxymethylallopurinol and N-(benzyloxycarbonyl)-DL-phenylalanine by the procedure described in Example 16. The analytically pure title compound crystallized with ¼ mole of water from methanol, m.p. 204°–205° C. (dec.).

EXAMPLE 28

1-(L-Leucyloxymethyl)allopurinol (hydrobromide)

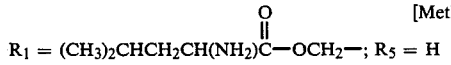 [Method (b)]

$R_1 = (CH_3)_2CHCH_2CH(NH_2)C\text{—}OCH_2\text{—}$; $R_5 = H$

The compound was prepared from 1-hydroxymethylallopurinol and N-(benzyloxycarbonyl)-L-leucine by essentially the same procedure as described in Example 16. The analytically pure title compound crystallized from methanol-acetonitrile with 1 mole of water, m.p. 215°–217° C. (dec.).

EXAMPLE 29

1-(N-Butylcarbamoyl)allopurinol

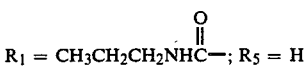 [Method (g)]

$R_1 = CH_3CH_2CH_2NHC\text{—}$; $R_5 = H$

A mixture of allopurinol (2.7 g, 20 mmole), triethylamine (0.2 ml), butylisocyanate (3 g, 30 mmole) in N,N-dimethylformamide was stirred at 90° C. for 2 hours. Upon cooling 1.05 g of the title compound precipitated. The crude product was recrystallized from N,N-dimethylformamide-ethanol, m.p. >270° C.

EXAMPLE 30

1-[3-(N,N-Diethylcarbamoyl)propionyloxymethyl]allopurinol

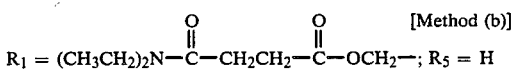 [Method (b)]

$R_1 = (CH_3CH_2)_2N\text{—}C\text{—}CH_2CH_2\text{—}C\text{—}OCH_2\text{—}$; $R_5 = H$ A mixture of 1-hydroxymethylallopurinol (1.47 g; 8.8 mmole), 3-(N,N-diethylcarbamoyl)propionic acid (1.53 g; 8.8 mmole), N,N'-dicyclohexylcarbodiimide (1.8 g; 8.8 mmole), and 4-toluenesulfonic acid (100 mg) in pyridine (30 ml) was stirred at room temperature for 24 hours. Methylene chloride (60 ml) was added, the mixture was filtered, and the filtrate evaporated in vacuo. The residue was extracted with warm methylene chloride (50 ml) and the methylene chloride was evaporated. The residue was recrystallized from ethyl acetate yielding 0.71 g (25%); m.p. 128°–131° C.

EXAMPLE 31

1-(Glycyloxymethyl)allopurinol (hydrochloride)

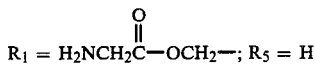 [Method (b)]

$R_1 = H_2NCH_2C\text{—}OCH_2\text{—}$; $R_5 = H$

The compound was prepared from 1-hydroxymethylallopurinol and N-(tert.butyloxycarbonyl)glycine by the same procedure as described in Example 16. The tert.butyloxycarbonyl-protecting group was removed with 1N hydrochloric acid. The title compound melted at 192°–195° C. (dec.).

TABLE 1

¹H NMR and UV spectral data, and HPLC chromatographic capacity factors of various allopurinol prodrugs

| Compound | ¹H NMR (δ) H(3) | and H(6) | λ_max(nm) (in pH 5.0 buffer) | Chromatographic capacity factor (k') |
|---|---|---|---|---|
| 1-(Acetyl)allopurinol[a] | 8.30 | 8.38 | 274 | 1.05[c] |
| 1-(Propionyl)allopurinol[a] | 8.30 | 8.37 | 274 | 0.66[d] |
| 1-(Butyryl)allopurinol[a] | 8.32 | 8.40 | 274 | 1.10[d] |
| 1-(Benzoyl)allopurinol[a] | 8.32 | 8.46 | 250,280(sh) | 1.20[d] |
| 1-(Chloroacetyl)allopurinol[a] | 8.29 | 8.39 | 274 | n.d. |
| 1-(Acetyloxymethyl)allopurinol[a] | 8.20 | 8.22 | 251 | 0.30[d] |
| 1-(Butyryloxymethyl)allopurinol[a] | 8.20 | 8.23 | 251 | 0.85[d] |
| 1-(Pivaloyloxymethyl)allo- | 8.19 | 8.23 | 251 | 1.50[d] |

TABLE 1-continued

¹H NMR and UV spectral data, and HPLC chromatographic capacity factors of various allopurinol prodrugs

| Compound | ¹H NMR (δ) H(3) | and H(6) | $\lambda_{max}(nm)$ (in pH 5.0 buffer) | Chromatographic capacity factor (k') |
|---|---|---|---|---|
| purinol[a] | | | | |
| 1-(Benzoyloxymethyl)allopurinol[a] | 8.45 | 8.49 | 234 | 2.00[d] |
| 1-(Nicotinoyloxymethyl)allopurinol[a] | 8.41 | 8.48 | 251 | 0.67[d] |
| 1-(Chloroacetoxymethyl)-allopurinol[a] | 8.31 | 8.33 | 251 | n.d. |
| 1-(DL-Alanyloxymethyl)-allopurinol[b] | 8.38 | 8.42 | 251 | 1.37[c] |
| 1-(DL-N,N—Diethylalanyloxymethyl)allopurinol[b] | 8.36 | 8.45 | 251 | 17.1[c] |
| 1-(N,N—Dimethylglycyloxymethyl)allopurinol[b] | 8.28 | 8.34 | 251 | 4.00[c] |
| 1-(N,N—Diethylglycyloxymethyl)allopurinol[b] | 8.27 | 8.32 | 251 | 12.0[c] |
| 1-(N,N—Dipropylglycyloxymethyl)allopurinol[b] | 8.34 | 8.40 | 251 | >60[c] |
| 1-[4-(N,N—Dimethylamino)-butyryloxymethyl]allopurinol[b] | 8.29 | 8.35 | 251 | n.d. |
| 2-(Butyryloxymethyl)allopurinol[a] | 8.06 | 8.78 | 261 | 0.65[d] |
| 2-(Pivaloyloxymethyl)allopurinol[a] | 8.08 | 8.70 | 261 | 1.07[d] |
| 1,5-bis(Butyryloxymethyl)-allopurinol[a] | 8.28 | 8.62 | 251 | 4.82[d] |
| 1,5-bis(Pivaloyloxymethyl)-allopurinol[a] | 8.29 | 8.64 | 251 | 13.8[d] |
| 2,5-bis(Butyryloxymethyl)-allopurinol[a] | 8.40 | 8.82 | 259 | 3.37[d] |
| 2,5-bis(Pivaloyloxymethyl)-allopurinol[a] | 8.41 | 8.85 | 259 | 9.9[d] |
| 1-(N,N—Dimethylglycyl)-allopurinol[b] | 8.45 | 8.46 | 279 | n.d. |
| 1-(Glycyloxymethyl)allopurinol[b] | 8.27 | 8.32 | 251 | 0.89[c] |
| 1-(Ethoxycarbonyloxymethyl)allopurinol[a] | 8.24 | 8.28 | 251 | n.d. |
| 1-(DL-Phenylglycyloxymethyl)allopurinol[b] | 8.15 | 8.20 | n.d. | n.d. |
| 1-(Succinyloxymethyl)-allopurinol[a] | 8.23 | 8.25 | 251 | n.d. |
| 2,5-bis(Acetyloxymethyl)-allopurinol[a] | 8.70 | 9.17 | 259 | n.d. |
| 2,5-bis(DL-Alanyloxymethyl)-allopurinol[b] | 8.51 | 8.97 | 259 | n.d. |
| 1-(L-Leucyloxymethyl)-allopurinol[b] | 8.32 | 8.36 | 251 | 0.80[d] |
| 1-(DL-Phenylalanyloxymethyl)allopurinol[b] | 8.28 | 8.30 | 251 | 1.05[d] |

[a]NMR in DMSO-$d_6$
[b]NMR in $D_2O$
[c]Mobile phase: 0.02 M phosphate buffer pH 7.4 - methanol (4:1 v/v)
[d]Mobile phase: 0.01 M acetate buffer pH 4.5 - methanol (1:1 v/v)
Column: 250 mm × 4 mm LiChrosorb RP-8 (Merck)
n.d. = Not determined

In-vitro cleavage of allopurinol derivatives

Reaction conditions.

Solutions of various derivatives of allopurinol in aqueous buffer solutions or 80% human plasma solutions (pH 7.4) were kept at 37° C. The initial concentration of the derivatives was in the range 0.01–0.1 mg/ml. At various times an aliquot of the solutions was withdrawn and analyzed by HPLC for remaining derivative as well as for allopurinol. For the plasma solutions the aliquot withdrawn was deproteinized with ethanol or trichloroacetic acid and after centrifugation, the clear supernatant was injected on HPLC.

Analytical method.

An HPLC method was used for the determination of allopurinol and its derivatives. In this method a reversed-phase LiChrosorb RP-8 column (250×4 mm) was eluated at ambient temperature with mixtures of methanol and 0.01M acetate buffer pH 4.5 or methanol and 0.03M phosphate buffer pH 7.0. The composition of the eluant was adjusted for each compound in order to provide an appropriate retention time. The flow rate was 1.2 ml/min and the column effluent was monitored spectrophotometrically at 252 nm or 274 nm. Quantitation of the compounds was done by measurement of peak heights.

Figure 1:
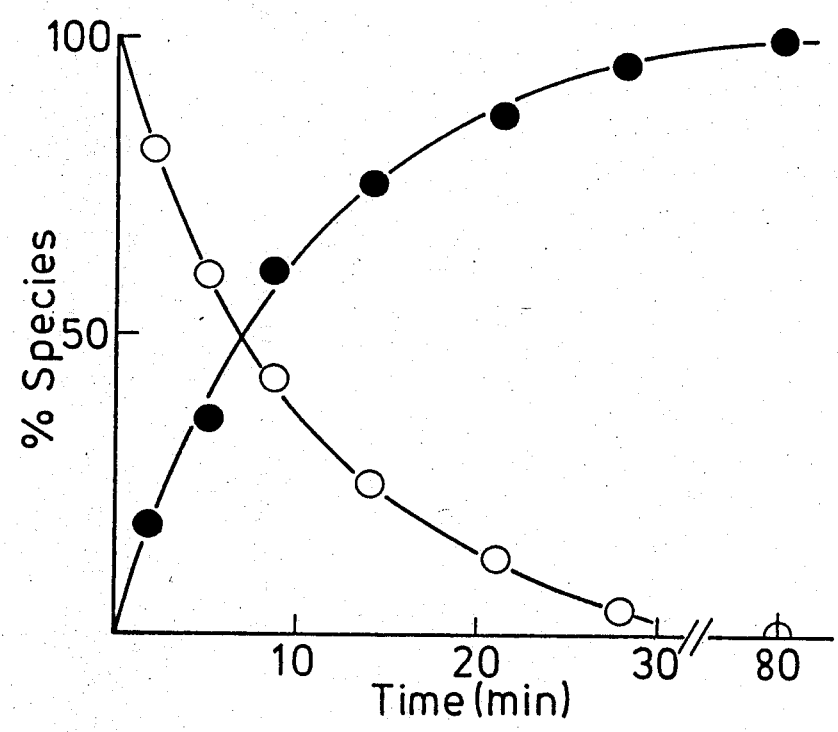
FIG. 1 shows the time-course of degradation of 1-(N,N-dimethylglycyloxymethyl)allopurinol (o) and the concomitant formation of allopurinol (•) in a 80% human plasma solution (pH 7.4) at 37° C.
Figure 2:
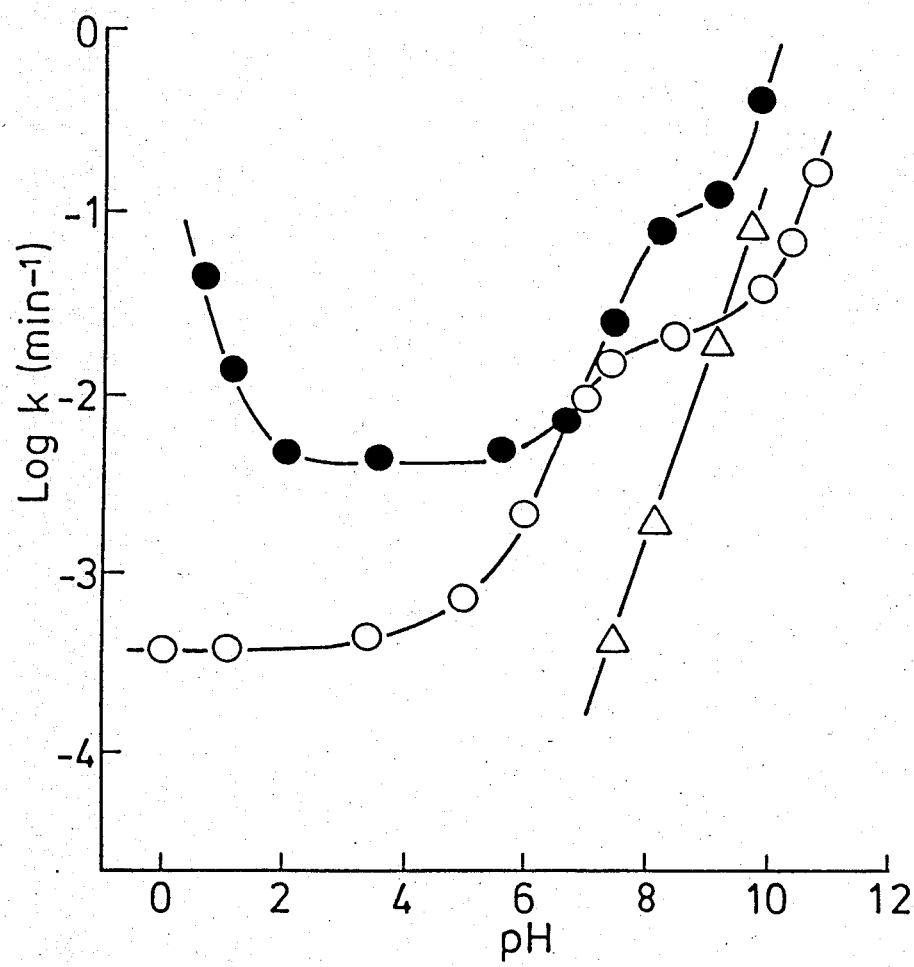
FIG. 2 shows plots of the logarithm of the observed pseudo-first-order rate constants against pH for the conversion of various allopurinol prodrugs to allopurinol in aqueous solution at 37° C.

A complete conversion of the derivatives to allopurinol was found to take place and in all cases, the cleavage of the derivatives displayed strict first-order kinetics. An example is shown in FIG. 1. The rate of hydrolysis varied greatly with pH of the solutions as illustrated in FIG. 2, showing the pH-rate profiles for some of the derivatives.

The half-times of allopurinol formation from various derivatives at physiological conditions of pH and temperature are given in Table 2. It can be seen that in the presence of human plasma the rate of degradation is strongly accelerated, thus showing the susceptibility of the derivatives to undergo conversion into the parent active compound at conditions simiar to those prevailing in vivo.

The water-solubility and lipophilicity of the allopurinol drugs

The apparent partition coefficients (P) for some allopurinol derivatives and allopurinol were measured using the widely used 1-octanol-water system. Similarly, the solubility of the derivatives in water or aqueous buffer solutions was determined. The values found for log P and the water-solubilities are listed in Table 3. The results obtained show clearly that by varying the pro-moieties of the derivatives or the type of derivative it is feasible to obtain prodrugs of allopurinol with varying and any desirable lipophilicity or water solubility. Thus, as demonstrated with the compound 1-(N,N-diethylglycyloxymethyl)allopurinol hydrochloride it is possible to obtain a prodrug form which at the same time possesses both a much higher aqueous solubility (i.e. a factor 5,000) and a higher lipophilicity than the parent compound.

Bioavailability of some allopurinol derivatives and allopurinol following rectal administration Suppositories were prepared of allopurinol and some derivatives of the present invention using Adepes solidus (Ph. Nord. 63) as the suppository base. Each suppository contained an amount of the appropriate compound (brought to the same particle size by sieving) equivalent to 25 mg of allopurinol. Some water-soluble derivatives were also formulated as micro-enemas, the solvent being a 0.5% aqueous solution of methylcellulose. The suppositories or micro-enemas were administered to rabbits. After drug administration, blood samples were taken at various times and the plasma fraction assayed for allopurinol and its major metabolite oxipurinol using the HPLC method described above.

FIG. 3 shows some representative plots of plasma oxipurinol concentrations versus time following rectal administration to rabbits. The results clearly demonstrate that the allopurinol derivatives exhibit a greatly enhanced bioavailability as compared with allopurinol which showed only a very low degree of absorption (<2% of the dose given). The plasma samples were also analyzed for intact allopurinol prodrugs but in all cases no measurable concentrations (<0.1 µg/ml) were observed. Thus, it is evident from the results that allopurinol prodrug forms of the present invention provide an efficient absorption of allopurinol after rectal administration in sharp contrast to the behaviour of allopurinol per se. Moreover, the above studies demonstrate that the prodrugs are converted back to allopurinol in vivo in accordance with the "prodrug" definition provided at the outset of this application.

In addition to these animal experiments, a micro-enema preparation of the hydrochloride salt of 1-(N,N-diethylglycyloxymethyl)allopurinol was administered to a healthy human volunteer. The dose given (2 ml of a 0.5% methylcellulose solution containing 118 mg/ml of the prodrug) corresponded to 100 mg of allopurinol. Urine was collected over 5 days and aliquots were assayed for allopurinol and oxipurinol by a specific HPLC assay. The total urinary excretion of allopurinol and oxipurinol was found to be 11 and 78 mg, respectively. Since it is known (Breithaupt & Tittel, 1982) that about 88% of a dose of allopurinol administered intravenously are recovered in the urine in the form of intact allopurinol (12%) and oxipurinol (76%) the result of the experiment indicates a virtually complete bioavailability of the parent drug from the prodrug derivative given rectally.

Furthermore, suppositories containing the hydrochloride salt of 1-(N,N-diethylglycyloxymethyl)allopurinol in an amount equivalent to 350 mg of allopurinol and made using Adeps solidus as the suppository base were administered rectally to five healthy human volunteers. After drug administration, blood samples were taken at various times and the plasma fraction assayed for allopurinol and oxipurinol by means of HPLC. FIG. 4 shows the average plasma data obtained. The same volunteers were also given a tablet preparation of allopurinol and from the plasma data obtained, the bioavailability of the suppository preparation containing the allopurinol prodrug was estimated to be 42% of that of the oral preparation.

Bioavailability after parenteral and oral administration

An aqueous solution of 1-(N,N-diethylglycyloxymethyl)allopurinol hydrochloride (1 ml containing 59 mg of the compound ~25 mg of allopurinol) was given intravenously to four rabbits. FIG. 5 shows the mean plasma oxipurinol concentration vs. time curve obtained along with the plasma concentration vs. time data observed after similar administration of 25 mg of allopurinol to the form of a 1% alkaline solution of sodium salt. The results of the experiment indicates an almost complete bioavailability of the parent drug from the prodrug derivative given intravenously.

A comparative absorption study was also made of allopurinol and the above mentioned prodrug following peroral administration. Each compound was given to a healthy human volunteer in a dose corresponding to 100 mg allopurinol, allopurinol in the form of a commercially available tablet and 1-(N,N-diethylglycyloxymethyl)allopurinol hydrochloride as a solution in water (236 mg in 10 ml). The total urinary excretion of allopurinol and oxipurinol was measured and found to correspond to 67% of the dose given for the allopurinol tablet and 92% for the preparation containing the prodrug derivative.

TABLE 2

Half-times ($t_{0.5}$) of the conversion of various allopurinol derivatives to allopurinol at 37° C.

| Compound | $t_{0.5}$ pH 7.4 buffer | 80% human plasma, min |
| --- | --- | --- |
| 1-(Butyryloxymethyl)allopurinol | 193 h | 9 |
| 2-(Butyryloxymethyl)allopurinol | 54 h | 22 |
| 1,5-bis(Butyryloxymethyl)allopurinol | 25 h | 22 |
| 2,5-bis(Butyryloxymethyl)allopurinol | 35 h | 32 |
| 1-(Acetoxymethyl)allopurinol | 87 h | 31 |
| 2,5-bis(Acetoxymethyl)allopurinol | 15 h | 51 |
| 1-(Benzoyloxymethyl)allopurinol | 237 h | 4 |
| 1-(Nicotinoyloxymethyl)allopurinol | 26 h | 21 |
| 1-(Glycyloxymethyl)allopurinol | 26 min | 9 |
| 1-(N,N—Dimethylglycyloxymethyl)-allopurinol | 72 min | 7 |
| 1-(N,N—Diethylglycyloxymethyl)-allopurinol | 49 min | 10 |
| 1-(DL-N,N—Diethylalanyloxymethyl)- | 21 min | 17 |

TABLE 2-continued

Half-times ($t_{0.5}$) of the conversion of various allopurinol derivatives to allopurinol at 37° C.

| Compound | $t_{0.5}$ pH 7.4 buffer | 80% human plasma, min |
|---|---|---|
| allopurinol | | |
| 1-(Acetyl)allopurinol | 26 min | 6 |
| 1-(Propionyl)allopurinol | 30 min | 4 |
| 1-(Butyryl)allopurinol | 36 min | 2.5 |
| 1-(Benzoyl)allopurinol | 20 min | 4 |
| 1-(DL-Alanyloxymethyl)allopurinol | 15 min | 11 |
| 1-(N,N—Dipropylglycyloxymethyl)-allopurinol | 50 min | 12 |
| 1-(DL-Phenylglycyloxymethyl)allopurinol | 20 min | 3 |
| 1-(L-Leucyloxymethyl)allopurinol | 17 min | 6 |
| 1-(Ethoxycarbonyloxymethyl)allopurinol | — | 20 |
| 1-(N,N—Dimethylglycyl)-allopurinol | 1.5 min | <1 |
| 1-(N—Butylcarbamoyl)-allopurinol | — | 90 |
| 1-(DL-Phenylalanyloxymethyl)-allopurinol | 40 min | 9 |
| 1[3-(N,N—Diethylcarbamoyl)-propionyloxymethyl]allopurinol | 81 h | 8.4 h |
| 1-(Chloroacetyl)allopurinol | <1 min | <1 |
| 1[4-(N,N—Dimethylamino)-butyryloxymethyl]allopurinol | 145 min | 140 |
| 2,5-bis(DL-Alanyloxymethyl)-allopurinol | <1 min | <1 |

TABLE 3

Water-solubilities (S) and partition coefficients (P) for allopurinol and various allopurinol prodrugs.

| Compound | $S^a$ (mg/ml) | log $P^b$ |
|---|---|---|
| Allopurinol | 0.50 | −0.55 |
| 1-(Pivaloyloxymethyl)allopurinol | 0.52 | 1.07 |
| 2-(Pivaloyloxymethyl)allopurinol | 1.7 | 0.79 |
| 1,5-bis(Pivaloyloxymethyl)allopurinol | 0.02 | 2.50 |
| 2,5-bis(Pivaloyloxymethyl)allopurinol | 0.045 | 2.34 |
| 1-(Butyryloxymethyl)allopurinol | 0.35 | 0.60 |
| 2-(Butyryloxymethyl)allopurinol | 1.5 | 0.33 |
| 1,5-bis(Butyryloxymethyl)allopurinol | 0.050 | 1.82 |
| 2,5-bis(Butyryloxymethyl)allopurinol | 0.094 | 1.60 |
| 1-(Acetoxymethyl)allopurinol | 0.58 | −0.35 |
| 2,5-bis(Acetoxymethyl)allopurinol | 2.9 | n.d. |
| 1-(Benzoyloxymethyl)allopurinol | 0.024 | 1.50 |
| 1-(Nicotinoyloxymethyl)allopurinol | 0.093 | 0.27 |
| 1-(Glycycloxymethyl)allopurinol hydrochloride | >500 | n.d. |
| 1-(DL-Alanyloxymethyl)allopurinol hydrobromide | >500 | n.d. |
| 1-(N,N—Dimethylglycyloxymethyl)-allopurinol hydrochloride | >500 | −0.49$^c$ |
| 1-(N,N—Diethylglycyloxymethyl)-allopurinol hydrochloride | >500 | 0.20$^c$ |
| 1-(N,N—Dipropylglycyloxymethyl)-allopurinol hydrochloride | >400 | 1.27$^c$ |
| 1-(DL-N,N—Diethylalanyloxymethyl)-allopurinol hydrochloride | >400 | 0.72$^c$ |
| 1-(DL-Phenylglycyloxymethyl)allopurinol hydrobromide | >200 | −0.15$^c$ |
| 1-(Acetyl)allopurinol | 0.75 | −0.35 |
| 1-(Propionyl)allopurinol | 0.30 | 0.30 |
| 1-(Butyryl)allopurinol | 0.11 | 0.85 |
| 1-(Benzoyl)allopurinol | 0.014 | 1.20 |
| 1-(Ethoxycarbonyloxymethyl)-allopurinol | n.d. | 0.21 |
| 1-(DL-Phenylalanyloxymethyl)-allopurinol hydrobromide | >200 | 0.40$^c$ |
| 1-(L-Leucyloxymethyl)allopurinol hydrobromide | >400 | 0.19$^c$ |
| 1-[3-N,N—Diethylcarbamoyl)-propionyloxymethyl]allopurinol | 33 | −0.22 |
| 1-(N,N—Dimethylglycyl)allopurinol | >200 | n.d. |

TABLE 3-continued

Water-solubilities (S) and partition coefficients (P) for allopurinol and various allopurinol prodrugs.

| Compound | $S^a$ (mg/ml) | log $P^b$ |
|---|---|---|
| hydrochloride | | |

$^a$At 21 ± 1° C.
$^b$Between octanol and water
$^c$Between octanol and a borate buffer pH 8.0
n.d. = not determined

References Cited

Appelbaum, S. J., M. Mayersohn, D. Perrier & R. T. Dorr: Drug Intell. Clin. Pharm. 14, (1980), p. 789.

Appelbaum, S. J. Mayersohn, R. T. Dorr & D. Perrier: Cancer Chemother. Pharmacol. 8, (1982), p. 93.

Bansal, P. C., I. H. Pitman & T. Higuchi: J. Pharm. Sci. 70, (1981), p. 855.

Bergmann, F., Frank, A. & Neimann, Z.: J. Chem. Soc. Perkin Trans I, (1979), p. 2795.

Breithaupt, H. & M. Tittel: Eur. J. Clin. Pharmacol. 22, (1982), p. 77.

Bundgaard, H. & M. Johansen: Acta Pharm. Suec 18, (1981), p. 129.

Chang, S.-L., W. G. Kramer, S. Feldman, R. Ballentine & L. S. Frankel: Am. J. Hosp. Pharm. 38, (1981), p. 365.

Elion, G. B., A. Kovinsky, G. H. Hitchings, E. Metz & R. W. Rundles: Biochem. Pharmacol. 15, (1966), p. 863.

Elion, G. B.: Handbook Exp. Pharmacol. 51, (1978), p. 485.

Hussain, A. & J. H. Rytting: J. Pharm. Sci. 63, (1974), p. 798.

De Leede, L. G. J. & A. G. De Boer: Biopharm. Drug Disp. 2, (1981), p. 131.

De Leede, L. G. J., A. G. De Boer, S. L. van Velzen & D. D. Breimer: J. Pharmacokin, Biopharm. 10, (1982), p. 525.

"Remington's Pharmaceutical Sciences", Sixteenth Edition (1980), Mack Publishing Company, Easton.

Spector, T.: Biochem. Pharmacol. 26, (1977), p. 355. P & V F3449A jA 423449 PCT HRA/BM 1984 05 16

We claim:

1. A compound of the formula Ia or Ib

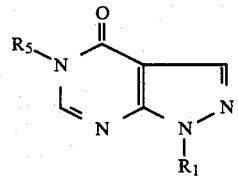

Ia

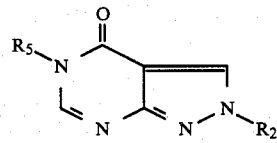

Ib wherein $R_1$ is a group of the formula II

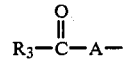

II wherein $R_3$ is $C_{1-8}$ alkyl; $C_{1-4}$ alkyl monosubstituted with chloro or bromo; phenyl; phenyl substituted with 1–3 substituents selected from chloro, bromo, $C_{1-4}$ alkyl, hydroxy, $C_{1-4}$ alkoxy, acetoxy, or phenoxy; phenyl $C_{1-4}$ alkyl in which the phenyl group may be substituted with 1–3 substituents selected from chloro, bromo, $C_{1-4}$ alkyl, hydroxy, $C_{1-4}$ alkoxy, acetoxy or phenoxy; or phenyl $C_{1-4}$ alkenyl in which the phenyl group may be substituted with 1–3 substituents selected from chloro, bromo, $C_{1-4}$ alkyl, hydroxy, $C_{1-4}$ alkoxy, acetoxy, or phenoxy; or $R_3$ is an aromatic 5- or 6-membered heterocyclic ring selected from pyridinyl, thienyl, thiazolyl, oxazolyl, imidazolyl, isoxazolyl, isothiazolyl, furanyl and pyrimidinyl; and A is a single bond or a group of the formula IIa

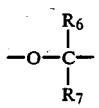

wherein the carbon atom is attached to the nitrogen atom of the parent ring system, and wherein $R_6$ and $R_7$ are the same or different and each represent hydrogen or have the same meaning as $R_3$ as defined above; or $R_1$ is a group of the formula III

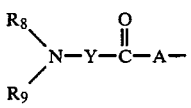

wherein $R_8$ and $R_9$ are the same or different and each represent hydrogen or have the same meaning as $R_3$ as defined above; or $R_8$ and $R_9$ together with the adjacent nitrogen form a 5- or 6-membered heterocyclic ring selected from piperidinyl, imidazolyl, pyrazolyl and piperazinyl; Y is a group of the formula IIIa

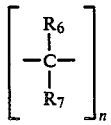

wherein n is an integer from 1 to 5; and A, $R_6$, and $R_7$ are as defined above;
or $R_1$ is a group of the formula IV

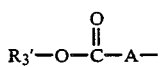

wherein A is as defined above and $R'_3$ has the same meaning as $R_3$ defined above, with the proviso that $R'_3$ is not ethyl when A is a bond;
or $R_1$ is a group of the formula VII

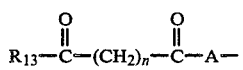

wherein n and A are as defined above, and $R_{13}$ is hydroxy or a group of the formula $-NR_8R_9$ wherein $R_8$ and $R_9$ are as defined above;
$R_2$ is any of the groups II, III, IV and VII as defined above with the proviso that A solely is the group IIa as defined above; and $R_5$ is hydrogen or has the same meaning as $R_2$ as defined above, or a pharmaceutically acceptable salt thereof.

2. A compound according to claim 1, wherein $R_1$ and $R_5$ are the same; or a pharmaceutically acceptable salt thereof.

3. A compound according to claim 2, wherein $R_1$ and $R_5$ are groups of the formulas II or III, wherein A is a group of formula IIa and Y is a group of formula IIIa; or a pharmaceutically acceptable salt thereof.

4. A compound according to claim 1, wherein $R_5$ is hydrogen and $R_1$ is a group of the formulas II, III, IV or VII; or a pharmaceutically acceptable salt thereof.

5. A compound according to claim 4, wherein $R_1$ is a group of the formulas II or III wherein Y is a group of formula IIIa or VII; or a pharmaceutically acceptable salt thereof.

6. A compound according to claim 5, wherein A is a group of formula IIa; or a pharmaceutically acceptable salt thereof.

7. A compound according to claim 6, wherein $R_1$ is a group of the formula III wherein A is a group of formula IIa and Y is a group of formula IIIa; or a pharmaceutically acceptable salt thereof.

8. A compound according to claim 7, wherein $R_1$ is N,N-dimethylglycyloxymethyl, N,N-diethylglycyloxymethyl, N,N-dipropylglycyloxymethyl, N,N-dimethylalanyloxymethyl, N,N-diethylalanyloxymethyl, phenylalanyloxymethyl, phenylglycyloxymethyl, or leucyloxymethyl; or a pharmaceutically acceptable salt thereof.

9. A compound according to claim 1, wherein $R_2$ and $R_5$ are the same; or a pharmaceutically acceptable salt thereof.

10. A compound according to claim 9, wherein $R_2$ and $R_5$ are groups of the formula III wherein A is a group of formula IIa and Y is a group of formula IIIa; or a pharmaceutically acceptable salt thereof.

11. A compound according to claim 1, wherein $R_5$ is hydrogen and $R_2$ is a group of the formula II wherein A is a group of formula IIa; or a pharmaceutically acceptable salt thereof.

12. A compound according to claim 1, selected from the group consisting of 1-(butyryloxymethyl)allopurinol, 1-(N,N-dimethylglycyloxymethyl)allopurinol, 1-(N,N-diethylglycyloxymethyl)allopurinol, 1-(N,N-dipropylglycyloxymethyl)allopurinol, 1-(DL-N,N-dimethylalanyloxymethyl)allopurinol, 1-(DL-N,N-diethylalanyloxymethyl)allopurinol, 1-(L-phenylalanyloxymethyl)allopurinol, 1-(L-leucyloxymethyl)allopurinol, 1-(L-valyloxymethyl)allopurinol and 1-(DL-N,N-dimethylphenylalanyloxymethyl)allopurinol; or a pharmaceutically acceptable salt thereof.

13. A pharmaceutical composition for rectal, parenteral, or oral use in the prevention and treatment of hyperuricemic states such as gout comprising a pharmaceutically acceptable carrier or excipient in combination with a compound of the formula I'a or Ib

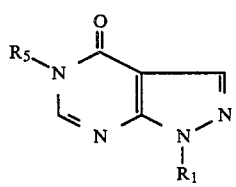

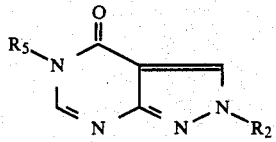

wherein $R_1$ is a group of the formula II

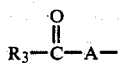

wherein $R_3$ is $C_{1-8}$ alkyl; $C_{1-4}$ alkyl monosubstituted with chloro or bromo; phenyl; phenyl substituted with 1–3 substituents selected from chloro, bromo, $C_{1-4}$ alkyl, hydroxy, $C_{1-4}$ alkoxy, acetoxy, or phenoxy; phenyl $C_{1-4}$ alkyl in which the phenyl group may be substituted with 1–3 substituents selected from chloro, bromo, $C_{1-4}$ alkyl, hydroxy, $C_{1-4}$ alkoxy, acetoxy or phenoxy; or phenyl $C_{1-4}$ alkenyl in which the phenyl group may be substituted with 1–3 substituents selected from chloro, bromo, $C_{1-4}$ alkyl, hydroxy, $C_{1-4}$ alkoxy, acetoxy, or phenoxy; or $R_3$ is an aromatic 5- or 6-membered heterocyclic ring selected from pyridinyl, thienyl, thiazolyl, oxazolyl, imidazolyl, isoxazolyl, isothiazolyl, furanyl and pyrimidinyl; and A is a single bond or a group of the formula IIa

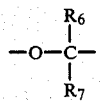

wherein the carbon atom is attached to the nitrogen atom of the parent ring system, and wherein $R_6$ and $R_7$ are the same or different and each represent hydrogen or have the same meaning as $R_3$ as defined above; or $R_1$ is a group of the formula III

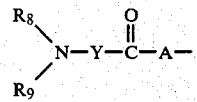

wherein $R_8$ and $R_9$ are the same or different and each represent hydrogen or have the same meaning as $R_3$ as defined above; or $R_8$ and $R_9$ together with the adjacent nitrogen form a 5- or 6-membered heterocyclic ring selected from piperidinyl, imidazolyl, pyrazolyl and piperazinyl; Y is a group of the formula IIIa

wherein n is an integer from 1 to 5; and A, $R_6$, and $R_7$ are as defined above;
or $R_1$ is a group of the formula IV

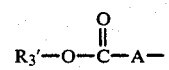

wherein A is as defined above and $R'_3$ has the same meaning as $R_3$ defined above;
or $R_1$ is a group of the formula VII

wherein n and A are as defined above, and $R_{13}$ is hydroxy or a group of the formula $-NR_8R_9$ wherein $R_8$ and $R_9$ are as defined above;
$R_2$ is any of the groups II, III, IV, and VII as defined above with the proviso that A solely is the group IIa as defined above; and $R_5$ is hydrogen or has the same meaning as $R_2$ as defined above; or a pharmaceutically acceptable salt thereof.

14. A method for treating and preventing hyperuricemic states comprising administering an amount effective in lowering the level of uric acid, of a compound according to any one of claims 1–12 to a warm-blooded animal.

15. A method for treating and preventing hyperuricemic states comprising administering an amount effective in lowering the level of uric acid of the composition of claim 13 to a warm-blooded animal.

16. The method of claim 15, wherein said composition is administered orally.

17. The method of claim 15, wherein said composition is administered rectally.

* * * * *